US011266672B2

(12) United States Patent
Miyano et al.

(10) Patent No.: US 11,266,672 B2
(45) Date of Patent: Mar. 8, 2022

(54) PHARMACEUTICAL COMPOSITION FOR TREATING AND/OR PREVENTING CANCER

(71) Applicant: TORAY INDUSTRIES, INC., Tokyo (JP)

(72) Inventors: Atsuko Miyano, Kamakura (JP); Hiroko Sudo, Kamakura (JP); Aiko Takayama, Kamakura (JP); Taiga Arai, Kamakura (JP)

(73) Assignee: TORAY INDUSTRIES, INC., Tokyo (JP)

(*) Notice: Subject to any disclaimer, the term of this patent is extended or adjusted under 35 U.S.C. 154(b) by 72 days.

(21) Appl. No.: 16/073,244

(22) PCT Filed: Jan. 27, 2017

(86) PCT No.: PCT/JP2017/003059
§ 371 (c)(1),
(2) Date: Jul. 26, 2018

(87) PCT Pub. No.: WO2017/131208
PCT Pub. Date: Aug. 3, 2017

(65) Prior Publication Data
US 2019/0046551 A1 Feb. 14, 2019

(30) Foreign Application Priority Data

Jan. 28, 2016 (JP) ............... JP2016-014379
Jun. 23, 2016 (JP) ............... JP2016-124328

(51) Int. Cl.
C12N 15/113 (2010.01)
A61K 31/7052 (2006.01)
A61K 31/7088 (2006.01)
A61K 31/7105 (2006.01)
A61K 31/713 (2006.01)
A61K 48/00 (2006.01)
C12N 15/11 (2006.01)
A61P 35/00 (2006.01)
C12N 15/861 (2006.01)

(52) U.S. Cl.
CPC ...... *A61K 31/7052* (2013.01); *A61K 31/7088* (2013.01); *A61K 31/713* (2013.01); *A61K 31/7105* (2013.01); *A61K 48/00* (2013.01); *A61P 35/00* (2018.01); *C12N 15/11* (2013.01); *C12N 15/111* (2013.01); *C12N 15/113* (2013.01); *C12N 15/861* (2013.01); *C12N 2310/141* (2013.01); *C12N 2320/30* (2013.01)

(58) Field of Classification Search
CPC ............ A61K 31/7052; A61K 31/7088; A61K 31/7105; A61K 31/713; A61K 48/00; C12N 15/11; C12N 15/111; C12N 15/113; C12N 15/861; C12N 2320/30; C12N 2310/141; A61P 35/00
See application file for complete search history.

(56) References Cited

U.S. PATENT DOCUMENTS

| 2005/0159381 | A1* | 7/2005 | McSwiggen ....... A61K 49/0008 514/44 A |
| 2014/0315983 | A1* | 10/2014 | Brown ................. A61K 31/713 514/44 A |
| 2015/0337332 | A1* | 11/2015 | Ruohoa-Baker ..... C12N 15/113 514/44 R |
| 2017/0107581 | A1 | 4/2017 | Kawauchi et al. |
| 2017/0114124 | A1* | 4/2017 | Wu ....................... C07K 16/18 |
| 2017/0130273 | A1 | 5/2017 | Sudo et al. |
| 2017/0130275 | A1 | 5/2017 | Kondou et al. |
| 2017/0275699 | A1 | 9/2017 | Kawauchi et al. |

FOREIGN PATENT DOCUMENTS

| JP | 2014-503553 A | 2/2014 | |
| WO | WO 2011/029903 A1 | 3/2011 | |
| WO | WO 2012/096573 A1 | 7/2012 | |
| WO | WO 2012/121178 A1 | 9/2012 | |
| WO | WO-2014012081 A2 * | 1/2014 | ............... C07H 1/00 |
| WO | WO 2014/071205 A1 | 5/2014 | |

(Continued)

OTHER PUBLICATIONS

International Search Report for PCT/JP2017/003059 (PCT/ISA/210) dated Apr. 4, 2017.
Kojima et al., "MicroRNA Markers for the Diagnosis of Pancreatic and Biliary-Tract Cancers", PLoS ONE, vol. 10, No. 2, 2015, 22 pages.
Written Opinion of the International Searching Authority for PCT/JP2017/003059 (PCT/ISA/237) dated Apr. 4, 2017.

* cited by examiner

*Primary Examiner* — J. E. Angell
(74) *Attorney, Agent, or Firm* — Birch, Stewart, Kolasch & Birch, LLP

(57) ABSTRACT

The present invention provides a novel pharmaceutical composition for treating and/or preventing cancer comprising, as an active ingredient, a polynucleotide derived from various miRNAs associated with cancer, a combination drug of the pharmaceutical composition and another antitumor agent, and a method for treating or preventing cancer in a subject having the cancer using the pharmaceutical composition or the combination drug. The present invention relates to a pharmaceutical composition for treating and/or preventing cancer comprising, as an active ingredient, a polynucleotide comprising the nucleotide sequence as set forth in SEQ ID NO: 1, or a nucleotide sequence comprising a substitution of one nucleotide in the nucleotide sequence as set forth in SEQ ID NO: 1 (wherein when at least a part of the polynucleotide is DNA, uracil in a region corresponding to the DNA in the nucleotide sequence is replaced with thymine).

11 Claims, 10 Drawing Sheets
Specification includes a Sequence Listing.

(56) References Cited

FOREIGN PATENT DOCUMENTS

| WO | WO 2014/072468 A1 | 5/2014 |
| WO | WO 2015/182781 A1 | 12/2015 |
| WO | WO 2015/190542 A1 | 12/2015 |
| WO | WO 2015/190591 A1 | 12/2015 |
| WO | WO 2015/194627 A1 | 12/2015 |

A

B

A

B

PHARMACEUTICAL COMPOSITION FOR TREATING AND/OR PREVENTING CANCER

TECHNICAL FIELD

The present invention relates to a pharmaceutical composition for treating and/or preventing cancer comprising, as an active ingredient, a polynucleotide derived from microRNA.

BACKGROUND ART

MicroRNA (miRNA) is an RNA of 16 to 28 nucleotides that is not translated into a protein, and it is currently known that 2590 miRNAs are present in human according to the miRBase release 21 (http://www.mirbase.org/). In recent years, miRNAs have been receiving attention as molecules for suppressing in vivo expression of various genes. Each miRNA gene region is present on the genome, and is transcribed into a RNA precursor with hairpin loop by RNA polymerase II, and the RNA precursor is then cleaved by two types of dsRNA cleaving enzyme having RNase III cleavage activities that are called Drosha in the nucleus and Dicer in the cytoplasm, thereby forming a mature miRNA. It is known that the mature miRNA is taken into the protein complex called RISC and interacts with mRNAs of a plurality of target genes having its complementary sequence to suppress the expression of the genes (Non Patent Literature 1).

Certain types of miRNAs are suggested to be associated with human diseases including cancer, and particularly in cancer, for example, many miRNAs such as hsa-miR-8073, hsa-miR-6893-5p and hsa-miR-575 are known to be markers specific to pancreatic cancer in blood (Non Patent Literature 1 and Patent Literature 1).

Further, in addition to the miRNAs related to the growth of cancer cells, the presence of a miRNA which works in a direction of suppressing cancer cells is reported, suggesting a method for treating cancer utilizing the expression pattern of the miRNA. Specific examples of the known method include a method for treating diseases such as cancer by administering an activated serum comprising 153 miRNAs such as hsa-Let-7a and upregulating the miRNA (Patent Literature 2), a method for treating lung cancer using a body fluid comprising many miRNAs such as hsa-Let-7a (Patent Literature 3), and a method for treating blood cancer by administering antisense oligonucleotides of many miRNAs such as miR-1321 comprised in circulating exosomes in the body (Patent Literature 4).

Moreover, it is reported that miRNAs expressed in breast cancer cells, including hsa-miR-30a, hsa-miR-221-5p or hsa-miR-146a, have an effect of suppressing angiogenesis of normal blood vessels and these miRNAs can be utilized as therapeutic agents for tumors based on the effect (Patent Literature 5). However, in Patent Literature 5, only the effect of suppressing angiogenesis of normal blood vessels was experimentally confirmed, and the actual utility of the miRNAs as therapeutic agents for tumors cannot be recognized only based on the confirmation of the aforementioned effect. Accordingly, Patent Literature 5 discloses next to nothing about the actual utility of these miRNAs as therapeutic agents for tumors.

CITATION LIST

Patent Literature

Patent Literature 1: International Publication No. WO 2015/182781
Patent Literature 2: International Publication No. WO 2011/029903
Patent Literature 3: International Publication No. WO 2014/072468
Patent Literature 4: International Publication No. WO 2014/071205
Patent Literature 5: International Publication No. WO 2012/121178

Non Patent Literature

Non Patent Literature 1: Kojima M PLoS One. 10(2) (2015) "MicroRNA markers for the diagnosis of pancreatic and biliary-tract cancers"

SUMMARY OF INVENTION

Technical Problem

It is an object of the present invention to identify a miRNA exhibiting therapeutic and/or preventive effects, in common, on various types of cancers, among various cancer-relating miRNAs, and to provide a novel pharmaceutical composition for treating and/or preventing cancer comprising, as an active ingredient, a polynucleotide derived from the miRNA.

Solution to Problem

The present inventors conducted extensive studies to solve the aforementioned problem and have now found a novel polynucleotide, which suppresses the growth of cancer cells, among miRNAs with increased or decreased expression in body fluids or tissues of cancer patients, thereby completing the present invention.

Specifically, the present invention encompasses the following features (1) to (14).
(1) A pharmaceutical composition for treating and/or preventing cancer comprising, as an active ingredient, a polynucleotide comprising a nucleotide sequence of the following (a) or (b) as a nucleotide sequence on the 5'-terminal side:
(a) the nucleotide sequence as set forth in SEQ ID NO: 1, or
(b) a nucleotide sequence comprising a substitution of one nucleotide in the nucleotide sequence as set forth in SEQ ID NO: 1.
(2) The pharmaceutical composition according to the above (1), wherein the nucleotide sequence of (b) is a nucleotide sequence comprising a substitution of any one of nucleotides at positions 4 to 6 from the 5'-terminus of the nucleotide sequence as set forth in SEQ ID NO: 1.
(3) The pharmaceutical composition according to the above (1) or (2), wherein the polynucleotide is a polynucleotide comprising the nucleotide sequence as set forth in any one of SEQ ID NOs: 1 to 4 as a nucleotide sequence on the 5'-terminal side.
(4) The pharmaceutical composition according to any one of the above (1) to (3), wherein the polynucleotide is 8 to 60 nucleotides in length.
(5) The pharmaceutical composition according to any one of the above (1) to (4), wherein the polynucleotide comprises a nucleotide sequence of the following (c) or (d) on the 3'-terminal side of the nucleotide sequence as set forth in SEQ ID NO: 1:
(c) a nucleotide sequence as set forth in any one of SEQ ID NOs: 5 to 11, or
(d) a nucleotide sequence comprising a deletion, substitution, insertion, and/or addition of 1 to 5 nucleotides in the nucleotide sequence as set forth in any one of SEQ ID NOs: 5 to 11.
(6) The pharmaceutical composition according to any one of the above (1) to (5), wherein the polynucleotide comprises a nucleotide sequence as set forth in any one of SEQ ID NOs: 12 to 22.
(7) The pharmaceutical composition according to any one of the above (1) to (6), wherein the polynucleotide is single stranded or double stranded.
(8) The pharmaceutical composition according to any one of the above (1) to (7), wherein the polynucleotide is RNA.
(9) The pharmaceutical composition according to any one of the above (1) to (8), wherein the cancer is a solid cancer.
(10) The pharmaceutical composition according to the above (9), wherein the cancer is selected from the group consisting of breast cancer, kidney cancer, pancreatic cancer, colorectal cancer, lung cancer, brain tumors, stomach cancer, cervical cancer, ovarian cancer, prostate cancer, bladder cancer, esophagus cancer, liver cancer, fibrosarcomas, mast cell tumors, and melanomas.
(11) The pharmaceutical composition according to any one of the above (1) to (10), wherein the polynucleotide is inserted into a vector in an expressible manner in the form of DNA.
(12) The pharmaceutical composition according to any one of the above (1) to (11), wherein the polynucleotide is encapsulated into a carrier selected from the group consisting of non-cationic polymer carriers, liposome carriers, dendritic carriers, nano-material carriers, microparticle carriers, biostructural carriers, micelle carriers, polymer microparticles, and magnetic microparticles, or the polynucleotide is bound to the carrier.
(13) A combination drug for treating and/or preventing cancer comprising, as active ingredients, the pharmaceutical composition according to any one of the above (1) to (12), and an antitumor agent.
(14) A method for treating or preventing cancer in a subject who suffers or has suffered from the cancer, comprising administering the pharmaceutical composition according to any one of the above (1) to (12), or the combination drug according to the above (13), to the subject.

The present description includes the contents as disclosed in Japanese Patent Application Nos. 2016-014379 and 2016-124328 from which the present application claims priority.

Advantageous Effects of Invention

The pharmaceutical composition for treating and/or preventing cancer of the present invention effectively suppresses the growth of cancer cells, and therefore it is useful for treating or preventing cancer.

DESCRIPTION OF EMBODIMENTS

<Polynucleotide as Active Ingredient>

Figure 1:
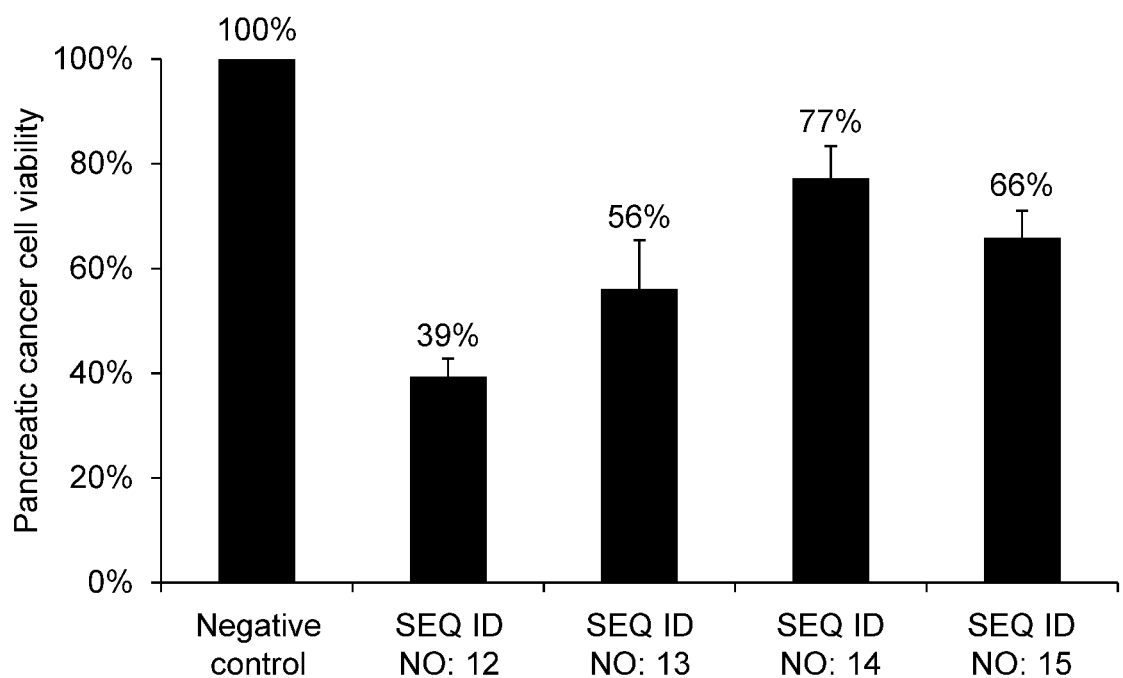
FIG. 1 This figure shows the ratios of viable cell counts (cell viability (%)) of the pancreatic cancer cell line Panc-1 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 into the cancer cells, relative to the viable cell count (100%) after introduction of a synthetic RNA being a negative control oligo into the cancer cells.

The pharmaceutical composition for treating and/or preventing cancer of the present invention comprises, as an active ingredient, a polynucleotide comprising the nucleotide sequence of ACCUGGCA (SEQ ID NO: 1) or a nucleotide sequence comprising a substitution of one nucleotide in the nucleotide sequence of ACCUGGCA (e.g., ACCUGCCA, ACCUUGCA, and ACCAGGCA, as set forth in SEQ ID NOs: 2, 3 and 4, respectively). Hereinafter, the polynucleotide as an active ingredient in the present invention will be described.

The nucleotide sequence as set forth in SEQ ID NO: 1 is a nucleotide sequence identified as a partial sequence on the 5' terminal side of hsa-miR-8073 (miRBase Accession No. MIMAT0031000), which is human miRNA; or as a partial sequence on the 5' terminal side of hsa-miR-221-5p (miRBase Accession No. MIMAT0004568), which is human miRNA. The nucleotide sequences as set forth in SEQ ID NOs: 2, 3 and 4 are nucleotide sequences identified as a partial sequence on the 5' terminal side of hsa-miR-4722-3p (miRBase Accession No. MIMAT0019837), a partial sequence on the 5' terminal side of hsa-miR-6841-3p (miRBase Accession No. MIMAT0027585), and a partial sequence on the 5' terminal side of hsa-miR-4645-5p (miRBase Accession No. MIMAT0019705), which are human miRNAs, respectively.

Among these miRNAs, hsa-miR-8073 had been known as a part of miRNA serving as a specific marker for pancreatic cancer (Kojima M PLoS One. 10(2) (2015) "MicroRNA markers for the diagnosis of pancreatic and biliary-tract cancers."). In addition, hsa-miR-221-5p had been known as a part of miRNA which is expressed in breast cancer cells and acts to suppress angiogenesis of normal blood vessels (WO2012/121178). In contrast, the present inventors have found for the first time that the miRNAs suppress the growth of pancreatic cancer cells and other cancer cells, and that the polynucleotides having the nucleotide sequences as set forth in SEQ ID NOs: 1 to 4, which are partial sequences of these miRNAs, play an important role in suppressing the growth of cancer cells. The nucleotide sequences as set forth in SEQ ID NOs: 2 to 4 correspond to nucleotide sequences comprising a substitution of one nucleotide in the nucleotide sequence as set forth in SEQ ID NO: 1.

Accordingly, the polynucleotide of the present invention is not particularly limited, as long as it comprises the nucleotide sequence as set forth in SEQ ID NO: 1, or a nucleotide sequence comprising a substitution of one nucleotide in the nucleotide sequence as set forth in SEQ ID NO: 1. A preferred example of the nucleotide sequence comprising a substitution of one nucleotide in the nucleotide sequence as set forth in SEQ ID NO: 1 is a nucleotide sequence comprising a substitution of any one of nucleotides at positions 4 to 6 from the 5'-terminus of the nucleotide sequence as set forth in SEQ ID NO: 1, such as, the nucleotide sequences as set forth in SEQ ID NOs: 2 to 4. Specifically, the polynucleotide of the present invention may be: either a polynucleotide consisting of the nucleotide sequence as set forth in SEQ ID NO: 1, or a nucleotide sequence comprising a substitution of one nucleotide in the nucleotide sequence as set forth in SEQ ID NO: 1 (e.g., SEQ ID NOs: 2 to 4); or a polynucleotide comprised of the nucleotide sequence as set forth in SEQ ID NO: 1, or a nucleotide sequence comprising a substitution of one nucleotide in the nucleotide sequence as set forth in SEQ ID NO: 1 (e.g., SEQ ID NOs: 2 to 4) and another nucleotide sequence added to the 5'-terminal and/or 3'-terminal side thereof. The polynucleotide of the present invention is preferably a polypeptide comprised of the nucleotide sequence as set forth in SEQ ID NO: 1, or a nucleotide sequence comprising a substitution of one nucleotide in the nucleotide sequence as set forth in SEQ ID NO: 1 (e.g., SEQ ID NOs: 2 to 4) and another nucleotide sequence added to the 3'-terminal side thereof. The polynucleotide of the present invention is preferably 8 to 60 nucleotides in length, and more preferably 16 to 28 nucleotides in length.

The nucleotide sequence to be added to the 3'-terminal side of the nucleotide sequence as set forth in SEQ ID NO: 1, or a nucleotide sequence comprising a substitution of one nucleotide in the nucleotide sequence as set forth in SEQ ID NO: 1 (e.g., SEQ ID NOs: 2 to 4), is preferably a nucleotide sequence comprising, as a partial sequence thereof, the following (a) or (b), more preferably a nucleotide sequence comprising the following (a) or (b) on the 5'-terminal side thereof, and further preferably a nucleotide sequence consisting of the following (a) or (b):

(a) a nucleotide sequence as set forth in any one of SEQ ID NOs: 5 to 11, or (b) a nucleotide sequence comprising a deletion, substitution, insertion, and/or addition of 1 to 5, preferably 1 to 4, more preferably 1 to 3, further preferably 1 or 2, and particularly preferably 1 nucleotide, in the nucleotide sequence as set forth in any one of SEQ ID NOs: 5 to 11.

In a preferred embodiment, the polynucleotide of the present invention may consist of the nucleotide sequence as set forth in any one of SEQ ID NOs: 1 to 4 and the nucleotide sequence of the above (a) or (b) added to the 3'-terminus or 5'-terminus thereof.

When at least a part of the polynucleotide of the present invention is DNA, uracil in a region corresponding to the DNA in the nucleotide sequence as set forth in any one of SEQ ID NOs: 1 to 11 is replaced with thymine.

Preferred specific examples of the polynucleotide, in which another nucleotide sequence is added to the 3'-terminal side of the nucleotide sequence as set forth in any one of SEQ ID NOs: 1 to 4, include a polynucleotide comprising the nucleotide sequence as set forth in any one of SEQ ID NOs: 12 to 20 (wherein when at least a part of the polynucleotide is DNA, uracil in a region corresponding to the DNA in the nucleotide sequences as set forth in SEQ ID NOs: 12 to 20 is replaced with thymine). Particularly preferred examples of such polynucleotides include polynucleotides consisting of the nucleotide sequences as set forth in SEQ ID NOs: 12 to 20 (wherein when at least a part of the polynucleotide is DNA, uracil in a region corresponding to the DNA in the aforementioned nucleotide sequences is replaced with thymine). Among these nine types of polynucleotides, the polynucleotides comprising the nucleotide sequences as set forth in SEQ ID NOs: 12 to 15 or 18 are known as miRNAs that have already been identified in humans. The names and miRBase Accession Nos. (registration numbers) of these miRNAs are as shown in Table 1.

TABLE 1

| SEQ ID NO: | Gene name | miRBase Accession No. |
| --- | --- | --- |
| 12 | hsa-miR-8073 | MIMAT0031000 |
| 13 | hsa-miR-221-5p | MIMAT0004568 |

TABLE 1-continued

| SEQ ID NO: | Gene name | miRBase Accession No. |
| --- | --- | --- |
| 14 | hsa-miR-4722-3p | MIMAT0019837 |
| 15 | hsa-miR-6841-3p | MIMAT0027585 |
| 20 | hsa-miR-4645-5p | MIMAT0019705 |
| 23 | hsa-miR-4454 | MIMAT0018976 |
| 24 | hsa-miR-575 | MIMAT0003240 |
| 25 | hsa-miR-1321 | MIMAT0005952 | hsa-miR-8073, which is a miRNA having the nucleotide sequence as set forth in SEQ ID NO: 12, is composed of the nucleotide sequence as set forth in SEQ ID NO: 1 as a nucleotide sequence from the 5' terminus (position 1) to the 8th nucleotide, and the nucleotide sequence as set forth in SEQ ID NO: 5 as the 9th and the subsequent remaining nucleotides. This miRNA has been known as a specific marker for pancreatic cancer, as described above. However, it has not been reported so far that compounds based on the sequence of a gene of this miRNA or a transcript thereof can suppress tumor cells.

hsa-miR-221-5p, which is a miRNA having the nucleotide sequence as set forth in SEQ ID NO: 13, is composed of the nucleotide sequence as set forth in SEQ ID NO: 1 as a nucleotide sequence from the 5' terminus (position 1) to the 8th nucleotide, and the nucleotide sequence as set forth in SEQ ID NO: 6 as the 9th and the subsequent remaining nucleotides. As mentioned above, it has been known that this miRNA is expressed in breast cancer cells and inhibits the angiogenesis of normal blood vessels, but it has not been reported so far that compounds based on the sequence of a gene of this miRNA or a transcript thereof can suppress tumor cells.

hsa-miR-4722-3p, which is a miRNA having the nucleotide sequence as set forth in SEQ ID NO: 14, is composed of the nucleotide sequence as set forth in SEQ ID NO: 2 as a nucleotide sequence from the 5' terminus (position 1) to the 8th nucleotide, and the nucleotide sequence as set forth in SEQ ID NO: 7 as the 9th and the subsequent remaining nucleotides. This miRNA has been identified by the method described in Persson H et al., 2011, Cancer Res., No. 71, pp. 78-86. However, it has not been reported so far that compounds based on the sequence of a gene of this miRNA or a transcript thereof can suppress tumor cells.

hsa-miR-6841-3p, which is a miRNA having the nucleotide sequence as set forth in SEQ ID NO: 15, is composed of the nucleotide sequence as set forth in SEQ ID NO: 3 as a nucleotide sequence from the 5' terminus (position 1) to the 8th nucleotide, and the nucleotide sequence as set forth in SEQ ID NO: 8 as the 9th and the subsequent remaining nucleotides. This miRNA has been identified by the method described in Ladewig E et al., 2012, Genome Res. No. 22, pp. 1634-1645. However, it has not been reported so far that compounds based on the sequence of a gene of this miRNA or a transcript thereof can suppress tumor cells.

hsa-miR-4645-5p, which is a miRNA having the nucleotide sequence as set forth in SEQ ID NO: 20, is composed of the nucleotide sequence as set forth in SEQ ID NO: 4 as a nucleotide sequence from the 5' terminus (position 1) to the 8th nucleotide, and the nucleotide sequence as set forth in SEQ ID NO: 10 as the 9th and the subsequent remaining nucleotides. This miRNA has been identified by the method described in Persson H et al., 2011, Cancer Res., No. 71, pp. 78-86. However, it has not been reported so far that compounds based on the sequence of a gene of this miRNA or a transcript thereof can suppress tumor cells.

A polynucleotide consisting of the nucleotide sequence as set forth in SEQ ID NO: 16 is an artificial polynucleotide in which the nucleotide sequence (SEQ ID NO: 7) of the 9th and the subsequent remaining nucleotides counted from the 5'-terminus of the above-described hsa-miR-4722-3p (SEQ ID NO: 14) is fused to the 3'-terminal side of the nucleotide sequence as set forth in SEQ ID NO: 1. Also, a polynucleotide consisting of the nucleotide sequence as set forth in SEQ ID NO: 17 is an artificial polynucleotide in which the nucleotide sequence (SEQ ID NO: 9) of the 9th and the subsequent remaining nucleotides counted from the 5'-terminus of hsa-miR-4454 is fused to the 3'-terminal side of the nucleotide sequence as set forth in SEQ ID NO: 1, and hsa-miR-4454 is a miRNA having the nucleotide sequence as set forth in SEQ ID NO: 23 that is known as a cancer marker but has not been reported to suppress tumor cells (Kojima M PLoS One. 10(2) (2015) "MicroRNA markers for the diagnosis of pancreatic and biliary-tract cancers"). Also, a polynucleotide consisting of the nucleotide sequence as set forth in SEQ ID NO: 18 is an artificial polynucleotide in which the nucleotide sequence (SEQ ID NO: 7) of the 9th and the subsequent remaining nucleotides counted from the 5'-terminus of the above-described hsa-miR-4722-3p (SEQ ID NO: 14) is fused to the 3'-terminal side of the nucleotide sequence as set forth in SEQ ID NO: 3. Also, a polynucleotide consisting of the nucleotide sequence as set forth in SEQ ID NO: 19 is an artificial polynucleotide in which the nucleotide sequence (SEQ ID NO: 9) of the 9th and the subsequent remaining nucleotides counted from the 5'-terminus of the above-described hsa-miR-4454 (SEQ ID NO: 23) is fused to the 3'-terminal side of the nucleotide sequence as set forth in SEQ ID NO: 3. Also, a polynucleotide consisting of the nucleotide sequence as set forth in SEQ ID NO: 21 is an artificial polynucleotide in which SEQ ID NO: 11, namely a nucleotide sequence formed by fusing the nucleotide sequence CUC to the 3'-terminal side of the nucleotide sequence as set forth in SEQ ID NO: 10, is fused to the 3'-terminal side of the nucleotide sequence as set forth in SEQ ID NO: 4. Also, a polynucleotide consisting of the nucleotide sequence as set forth in SEQ ID NO: 22 is an artificial polynucleotide in which the nucleotide sequence (SEQ ID NO: 5) of the 9th and the subsequent remaining nucleotides counted from the 5'-terminus of hsa-miR-8073 which is a miRNA having the nucleotide sequence as set forth in SEQ ID NO: 12, is fused to the 3'-terminal side of the nucleotide sequence as set forth in SEQ ID NO: 4.

The polynucleotide of the present invention may have any structure, as long as it exhibits the effects of treating and/or preventing cancer, and may have, for example, a single-stranded structure, a double-stranded structure, or a multiple-stranded structure such as a triple- or more-stranded structure. The present polynucleotide has preferably a single-stranded or double-stranded structure, and more preferably a single-stranded structure.

The polynucleotide of the present invention may be RNA, DNA or RNA/DNA (chimera), as long as it can exhibit the effects of treating and/or preventing cancer. With regard to the polynucleotide of the present invention, when the entire or a part of the nucleotide sequence corresponding to a sequence number shown in Sequence Listing is DNA, U (uracil) in the region corresponding to the DNA in the nucleotide sequence shown in Sequence Listing is replaced with T (thymine). The polynucleotide of the present invention is preferably RNA. Examples of types of RNA include mRNA, rRNA, non-coding RNA, siRNA, shRNA, snoRNA, snRNA, nkRNA (registered tradename), and PnkRNA (tradename), as well as the above-described miRNA. The RNA is preferably miRNA. The miRNA includes synthetic miRNA that is what is called a mimic, as well as naturally occurring miRNA.

The polynucleotide usable in the present invention can comprise at least one modified nucleotide analog. The nucleotide analog can be placed, for example, at the 5' terminus, 3' terminus, and/or inside of an RNA molecule. In particular, by incorporation of the modified nucleotide analog, the polynucleotide can be further stabilized.

The nucleotide analog is, for example, preferably a sugar- or backbone-modified ribonucleotide, and more preferably a ribonucleotide having a modified nucleic acid base, and more specifically, a ribonucleotide comprising a non-naturally occurring nucleic acid base. Examples of the non-naturally occurring nucleic acid base include, for example, uridine or cytidine modified at position 5, such as 5-methyluridine, 5-(2-amino)propyluridine, 5-methyl-2-thiouridine, 5-bromouridine, or 6-azouridine, adenosine and guanosine modified at position 8, such as 8-bromoguanosine, deazanucleotide, or 7-deaza-adenosine; and O- and N-alkylated nucleotides, N6-methyladenosine, and universal bases.

A preferred sugar-modified ribonucleotide may be a ribonucleotide having a substitution of a 2'-OH group in a sugar moiety with a group selected from the group consisting of H, OR, halo, SH, SR, $NH_2$, NHR, $NR_2$ and CN, or a ribonucleotide comprising a 2'-O, 4'-C methylene bridge or an ethylene bridge (for example, LNA or ENA), wherein R is C1 to C6 alkyl, alkenyl or alkynyl, and halo is F, Cl, Br or I. Further, the modified sugar moiety in the sugar modified ribonucleotide may be mannose, arabinose, glucopyranose, galactopyranose, 4'-thioribose or another sugar; or a hetero ring or a carbon ring.

Examples of a preferred backbone-modified ribonucleotide include ribonucleotides having a substitution of a phosphoester group that binds to an adjacent ribonucleotide, with, for example, a phosphothioate-modified group, boranophosphate, 3'-(or 5')deoxy-3'-(or 5')aminophosphoramidate, hydrogen phosphonate, boranophosphate ester, phosphoramidate, alkyl, or aryl phosphonate and phosphotriester. Any of the above-described modifications may be used in combination.

<Carrier to be Used Together with the Polynucleotide as Active Ingredient>

The pharmaceutical composition for treating and/or preventing cancer of the present invention may comprise a pharmaceutically acceptable carrier, in addition to the polynucleotide of the present invention. The pharmaceutically acceptable carrier is preferably a substance, which facilitates the transport of the polynucleotide of the present invention to target cells or tissues, does not stimulate a living body, and does not inhibit the activities and properties of the polynucleotide of the present invention, and it is also preferable that the carrier itself does not induce the production of harmful antibodies to individuals, to which the composition is administered. The size of carrier is preferably a size which does not permeate normal blood vessel walls but can permeate newborn blood vessels in cancer tissues. When a carrier is an approximate spheroid, the diameter of the carrier may be preferably a nano size of, for example, about 1 nm or more and less than 100 nm.

The carrier may encapsulate the polynucleotide of the present invention, or may movably bind to the polynucleotide of the present invention. The phase "movably bind to" refers to the electronic interaction between the carrier and one or more agents. The interaction is not limited, and may be in the form of any chemical bonds, including covalent bond, polar covalent bond, ionic bond, electrostatic bond, coordinate covalent bond, aromatic bond, hydrogen bond, and dipole or Van der Waals interaction.

The binding site of the polynucleotide of the present invention and the carrier is preferably on the 5' terminal side or on the 3' terminal side, and more preferably on the 5' terminal side.

Specific examples of the carrier include non-cationic polymer carriers, liposome carriers, dendrimer carriers, nano-material carriers, microparticle carriers, biostructural carriers, micelle carriers, polymer microparticles, and magnetic microparticles.

The non-cationic polymer carrier refers to a polymer that can encapsulate one or two or more agents therein, and/or can movably bind to such agent(s), and is, for example, anionic (i.e., negatively charged) or an electronically neutral and cotton-like or branched. The carrier may be in the form of microparticles or nanoparticles, or may also be water-soluble or water-insoluble, or biodegradable or non-biodegradable carrier. Preferred non-cationic polymer carriers are known to those skilled in the art. The non-cationic polymer carrier may include, for example, poly-L-glutamic acid (PGA), poly-(γ-L-glutamyl glutamine) (PGGA), poly-(γ-L-aspartyl glutamine) (PGAA) or poly-(lactide-co-glycolide) (PLGA); and a mixture of at least two polymers.

The liposome carrier has a lipid double layer structure comprising lipids attached to polar hydrophilic groups, which forms, in an aqueous medium, a substantially closed structure which can encapsulate one or two or more agents and/or can movably bind to the agent(s). The liposome carrier may comprise a single lipid double layer (i.e., unilamellar) or may also comprise a concentric lipid double layer consisting of two or three or more layers (i.e., multilamellar). The liposome carrier may have an approximate spherical or approximate elliptical shape. Preferred liposome carriers are known to those skilled in the art, and can be selected based on various properties such as the rigidity of the lipid double layer, the electronic charge of the lipid double layer and/or the compatibility of one or both of the agents with the liposome carrier. The liposome carrier may comprise, for example, natural phospholipids such as egg phosphatidylcholine, egg phosphatidylethanolamine, soy phosphatidylcholine, lecithin and sphingomyelin, synthetic phosphatidylcholine, lysophosphatidylcholine, phosphatidylglycerol, phosphatidic acid, phosphatidyl ethanolamine, dioctadecylamide glycylspermine, dioleoylphosphatidylethanolamine, N-1-2,3-dioleyloxypropyl-N,N,N-trimethylammonium chloride, 2,3-diolexyoloxy-N-2-sperminecarboxamidoethyl-N,N-dimethyl-1-propaneammonium trifluoroacetamide, phosphatidylserine, derivatives thereof, and PEGylated phospholipids.

The dendritic carrier refers to a dendrimer, a dendron, or derivatives thereof, which can encapsulate one or two or more agents, and/or can movably bind to the agent(s). The dendrimer refers to a macromolecule having a core and a plurality of branch-structured shells spreading from the core. The dendron is a type of dendrimer having branches spreading from a focal point. The dendritic carriers are commercially available or can be synthesized by methods known to those skilled in the art. The dendritic carrier may be at least partially hydrophobic or hydrophilic. The dendritic carrier may be cationic, or electronically neutral or anionic. The dendritic carrier may comprise a core molecule, and examples thereof include alkyl diamines such as ethylenediamine, 1,4-diaminobutane, 1,6-diaminohexane and 1,12-diaminodecane; amines such as ammonia; alkylimines such as cystamine and polyethyleneimine (PEI); and chlorinated phosphorus molecules such as cyclotriphosphazene and thiophosphoryl. The dendritic carrier may comprise alkylimines such as polypropyleneimine (PPI), tertiary amines such as polyamideamine (PAMAM), polyamino acids such as polylysine, and/or phenoxymethyl (methylhydrazono) (PMMH).

The nano-material carrier refers to a material having the longest dimension ranging from about 1 nm to about 100 nm, which can encapsulate one or two or more agents and/or can movably bind to the agent(s). Preferred nano-material carriers are known to those skilled in the art, and examples of the nano-material carrier may include a nanoparticle, nanopowder, nanocluster, nanocrystal, nanosphere, nanofiber, nanotube, nanocluster, nanocrystal, nanosphere, nanofiber, nanotube, nanogel, and/or nanorod. The examples of the substance constituting the nano-material carrier include poly-(lactide-co-glycolide) (PLGA), polyalkylcyanoacrylate (PACA), polyepsilon-caprolactone (PCL), polylactic acid (PLA), polyethyleneglycol (PEG), poly-N-vinylcaprolactam sodium acrylate, poly-N-isopropylacrylamide, and polyvinyl acetate. Further, in some aspects, the nano-material carrier may be fullerene, and the fulleren may include spherical fullerenes (e.g., C60), carbon nanotubes, and fullerene derivatives.

The microparticle carrier refers to a particle having the longest dimension ranging from about 100 nm to about 100 μm. The microparticle may have any shapes and any forms. Examples of the substance constituting the microparticle carrier include poly-(lactide-co-glycolide) (PLGA), polyalkylcyanoacrylate (PACA), polyepsilon-caprolactone (PCL), polylactic acid (PLA), PLGA, and polyethyleneglycol (PEG).

The biostructural carrier refers to a polymer or a compound, in which a large number of units in the biostructural carrier are amino acids and/or saccharides, and which can encapsulate one or two or more agents therein and/or movably bind to the agent(s). Preferred biostructural carriers are known to those skilled in the art, and may comprise any of sugars, monosaccharides, oligosaccharides, polysaccharides, cyclic polysaccharides, non-cyclic polysaccharides, linear polysaccharides, branched polysaccharides, amino acids, proteins, and peptides; and semisynthesized derivatives thereof. The biostructural carrier may comprise any of α-cyclodextrin, β-cyclodextrin, γ-cyclodextrin, methyl β-cyclodextrin, dimethyl-β-cyclodextrin, carboxymethyl-β-cyclodextrin, hydroxypropyl-β-cyclodextrin, sulfobutyl ether-β-cyclodextrin, tri-O-methyl-β-cyclodextrin, glucosyl-β-cyclodextrin, β1,3D glucan, β1,6 glucan, C-reactive protein, conalbumin, lactalbumin, ovalbumin, parvalbumin, serum albumin, technetium TC99m aggregated albumin, human serum albumin (HSA), bovine serum albumin (BSA), recombinant human serum albumin (rHSA), glucose (dextrose), fructose, galactose, xylose, ribose, sucrose, cellulose, cyclodextrin, and starch.

The micelle carrier has a micelle structure formed by lipids, such as any fat-soluble (or lipophilic) molecule, oil, wax, sterol, monoglyceride, diglyceride, triglyceride, phospholipid, etc. The micelle carrier may comprise any of polyalkylene glycols such as polyethylene glycol (PEG); polyamino acids such as polyaspartic acid and polyglutamic acid (PGA); poly-(γ-L-glutamyl glutamine) (PGGA), polyphenyleneoxide (PPO), poly(ε-caprolactone) (PCL), poly-(lactide-co-glycolide) (PLGA), and a diblock copolymer.

Further, the carrier may also be a conjugate, and may comprise a nucleotide linker, a non-nucleotide linker or a nucleotide/non-nucleotide complex linker, which links a sense region with an antisense region of a nucleic acid; polyethylene glycol; human serum albumin; and a ligand for a cell receptor, capable of inducing the cellular uptake. Additionally, the nucleotide linker may be a linker having 2 or more nucleotides in length, or may also be a nucleic acid aptamer.

The pharmaceutical composition for treating and/or preventing cancer comprising the polynucleotide of the present invention may further comprise at least one substance selected from pharmaceutically acceptable excipients, pharmaceutical carriers and diluents. The present polynucleotide can be formulated with a further added diluent, dispersant, surfactant, binder, lubricant and/or a mixture thereof, into any dosage forms including parenteral dosage forms such as injection dosage forms, or forms suitable for intrarectal, intranasal, local, subcutaneous, vaginal or other parenteral administration, or oral dosage forms such as pills, capsules, granules or tablets, or forms suitable for inhalation or infusion administration.

When the polynucleotide of the present invention is used as a liquid preparation, the carrier is preferably sterilized and suitable for a living body, and further, other common additives such as an antioxidant, a buffer solution and a bacteriostatic agent may also be added. Preferred additives include, but are not limited to, macromolecules that are large and slowly metabolized, such as proteins, polysaccharides, polylactic acid, polyglycolic acid, polymeric amino acids, amino acid copolymers, lipid aggregates, hydrogels, inactivated virus particles, and collagens. Further, a liquid preparation comprising the polynucleotide of the present invention may comprise liquids such as water, saline, sterilized water, Ringer's solution, buffered saline, albumin injection solution, dextrose solution, maltodextrin solution, glycerol or ethanol, and may also comprise auxiliary substances such as moistening agent, emulsifying agent, pH buffering substance and the like.

In the context of the present invention, the term "administration" means introduction of the polynucleotide of the present invention, or a pharmaceutical composition for treating and/or preventing cancer comprising, as an active ingredient, the polynucleotide of the present invention, to a patient by any suitable method. The administration includes the delivery of the polynucleotide of the present invention by a viral or non-viral technique, and transplantation of cells which express the polynucleotide of the present invention.

The administration can be carried out via various oral or parenteral administration routes, as long as the polynucleotide can reach a target tissue. For example, the administration can be carried out by an intraoral, intrarectal, local, intravenous, intraperitoneal, intramuscular, intraarterial, transdermal, intranasal, inhalation, intraocular, or intradermal route.

The dose varies depending on the purpose of administration, an administration method, type and size of a tumor, characteristics (sex, age, body weight, etc.) of a person to be administered (i.e., a subject). Typically, with regard to the dose, a drug is administered at a lower level and is then increased until the intended effect is achieved. A preferred dose of the polynucleotide of the present invention may range, but not limited to, for example, from 1 pmol to 100 nmol per kg of body weight; or from 0.001 to 0.25 mg per kg of body weight, or from 0.01 to 20 µg per kg of body weight, or from 0.10 to 5 µg per kg of body weight. Such doses are administered preferably 1 to 10 times, and more preferably 5 to 10 times.

<Suppression of Cancers by the Polynucleotide>

The polynucleotide of the present invention may be provided in a form of a polynucleotide introduced into cells. The phrase "introduced into cells" means the entry of a foreign polynucleotide into cells by transfection or transduction. The transfection refers to, for example, calcium phosphate-DNA co-precipitation, DEAE-dextran-mediated transfection, polybrene-mediated transfection, electroporation, microinjection, liposome fusion, Lipofectamine transfection, and protoplast fusion. The transduction means the transfer of a gene into other cells by means of infection using a virus or a viral vector particle (e.g., a vector based on adenovirus, adeno-associated virus, Sendai virus, or retrovirus (lentivirus, etc.)) or using a plasmid vector. The vector can comprise necessary elements (e.g., a promoter, etc.) for enabling the expression of the polynucleotide of the present invention, and can be prepared by known techniques (e.g., Sambrook and Russell, Molecular Cloning A Laboratory Manual ($4^{th}$ Ed., 2001), Cold Spring Harbor Laboratory Press, JP Patent Publication No. 2016-153403 A, JP Patent Publication No. 2016-025853 A). The cells into which the polynucleotide of the present invention has been introduced by such methods, can express the polynucleotide of the present invention at a high level. Thus, the cells can be utilized as a cell therapeutic agent for suppressing the growth of cancer when transplanted into cancer tissues.

<Type of Cancer>

The terms "tumor" and "cancer" are used in the context of the present invention to mean malignant neoplasms, and are used interchangeably. The cancer to be targeted includes, but is not particularly limited to, a solid cancer. Specific examples of the cancer to be targeted include cancers and cancer cells developed in, or derived from, the bladder, bone, bone marrow, brain, breast, colon/rectum, esophagus, digestive tract, gum, head, kidney, liver, lung, nasopharynx, neck, ovary, prostate, skin, stomach, testis, tongue, blood or uterus. Preferred examples of the cancer include breast cancer, kidney cancer, pancreatic cancer, colorectal cancer, lung cancer, brain tumor, stomach cancer, cervical cancer, uterine cancer, ovarian cancer, prostate cancer, bladder cancer, esophagus cancer, liver cancer, fibrosarcoma, mast cell tumor, and melanoma. Specific examples of these cancers include, but are not limited to, mammary gland cancer, complex mammary gland carcinoma, mammary gland malignant mixed tumor, intraductal papillary adenocarcinoma, lung adenocarcinoma, squamous cell carcinoma, small cell carcinoma, large cell carcinoma, glioma which is a neuroepithelial tissue tumor, ependymoma, neurocytoma, embryonal neuroectodermal tumor, schwannoma, neurofibroma, meningioma, chronic lymphocytic leukemia, lymphoma, GI lymphoma, digestive lymphoma, small to medium cell lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal cancer, invasive pancreatic ductal cancer, adenocarcinoma of pancreatic cancer, acinic cell carcinoma, adenosquamous carcinoma, giant cell tumor, intraductal papillary mucinous neoplasm, mucinous cystadenocarcinoma, pancreatoblastoma, serous cystadenocarcinoma, solid papillary cancer, gastrinoma, glucagonoma, insulinoma, multiple endocrine adenomatosis, non-functional islet cell tumor, somatostatinoma, and VIPoma.

Moreover, preferred subjects to be targeted in the present invention are mammals, including primates such as human, livestock such as cow, pig, sheep and horse, companion animals such as dog and cat, and mammals in a zoo. Among others, human is preferable.

In the present invention, the polynucleotide of the present invention, or the pharmaceutical composition for treating and/or preventing cancer according to the present invention, can be administered to the subject for treating and/or preventing cancer.

<Type of Antitumor Agent>

In the present invention, a drug (referred to as a "combination drug") of a pharmaceutical composition for treating and/or preventing cancer comprising, as an active ingredient, the polynucleotide of the present invention, in combination with another (typically, known) antitumor agent, or with a pharmaceutical composition comprising another antitumor agent, can be administered to a subject in combination, and thereby preferably increasing the antitumor effects. The pharmaceutical composition for treating and/or preventing cancer according to the present invention and another antitumor agent (or a pharmaceutical composition comprising another antitumor agent) can be administered to a subject, simultaneously or separately. In the case of the separate administration, either the pharmaceutical composition or the antitumor agent may be administered earlier or later, and the dosing interval, doses, administration routes and the numbers of doses can be determined appropriately by a medical specialist. Another dosage form of the drug to be simultaneously administered include, for example, a pharmaceutical composition also referred to as a "mixed drug" prepared by mixing and formulating the pharmaceutical composition for treating and/or preventing cancer according to the present invention with an antitumor agent in a pharmaceutically acceptable carrier (or medium).

Examples of the antitumor agent include the following antitumor agents known in literatures or the like.

Examples of the antitumor agent as an alkylating agent such as Thiotepa and cyclophosphamide include: alkyl sulfonates such as (i.e., "including") busulfan, improsulfan, and piposulfan; aziridines such as benzodopa, carboquone, meturedopa, and uredopa; ethyleneimines such as Altretamine, triethyleneamine, triethylenephosphoramide, triethilenethiophosphoramide, and trimethylolamine; acetogenins such as bullatacin and bullatacinone; camptothecin; bryostatin; callystatin; cryptophycin 1, and cryptophycin 8; dolastatin; duocarmycin; eleutherobin; pancratistatin; sarcodictyin; spongistatin; nitrogen mustards such as chlorambucil, chlornaphazine, cholophosphamide, and estramustine; ifosfamide, mechlorethamine, mechlorethamine oxide hydrochloride, melphalan, temozolomide, novembichin; fenesterin, prednimustine, trofosfamide, uracil mustard; and nitrosoureas such as bendamustine, carmustine, chlorozotocin, streptozocin, fotemustine, lomustine, nimustine, and ranimnustine.

Examples of the antitumor agent as an anticancer antibiotic include calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, daunorubicin, detorubicin, 6-diazo-5-oxo-L-norleucine, adriamycin (doxorubicin), bleomycin, aclarbicin, amrubicin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, and zorubicin.

Examples of the antitumor agent as an antimetabolite include: folic acid analogs such as denopterin, pteropterin, methotrexate, trimetrexate, and pemetrexed; purine analogs such as fludarabine, 6-mercaptopurine, thiamiprine, thioguanine, cladribine, and clofarabine; pyrimidine analogs such as ancitabine, azacitidine, 6-azauridine, carmofur, cytarabine, dideoxyuridine, doxifluridine, enocitabine, floxuridine, trifluridine, capecitabine, 5-FU, gemcitabine, S-1, and tegafur; and hydroxycarbamide and nelarabine.

Examples of the antitumor agent as a hormone preparation include anastrozole, bicalutamide, degarelix, estramustine, exemestane, flutamide, fulvestrant, goserelin, letrozole, leuplin, medroxyprogesterone, mepitiostane, octreotide, tamoxifen, and toremifene, and for example, androgen preparations such as calusterone, drostanolone propionate, epitiostanol, mepitiostane, testolactone, and enzalutamide; antiadrenal preparations such as aminoglutethimide, mitotane, and trilostane; and frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, epothilone, etoglucid, lenthinan, lonidamine, maytansine, ansamitocine, abiraterone, mitoguazone, mitoxantrone, mopidanmol, nitraerine, pentostatin, phenamet, pirarubicin, losoxantrone, podophyllic acid, 2-ethyl hydrazide, procarbazine, razoxane, rhizoxin, sizofiran, spirogermanium, tenuazonic acid, triaziquone, roridin A, anguidine, urethane, vindesine, dacarbazine, mannomustine, mitobronitol, mitolactol, pipobroman, gacytosine, arabinoside, BCG, Krestin, and picibanil.

Examples of the antitumor agent as another anticancer agent such as those derived from plants include docetaxel, etoposide, teniposide, irinotecan, nogitecan, paclitaxel, cabazitaxel, vinblastine, vincristine, vindesine, vinorelbine, carboplatin, cisplatin, dacarbazine, eribulin, L-asparaginase, miriplatin, mitoxantrone, nedaplatin, oxaliplatin, pentostatin, procarbazine, arsenic trioxide, sobuzoxane, tamibarotene, mitoxantrone, novantrone, edatrexate, ibandronate, topoisomerase inhibitor, difluoromethylornithine (DMFO), and retinoic acid.

Examples of the antitumor agent as a molecular target drug include afatinib, axitinib, alectinib, bevacizumab, cetuximab, crizotinib, erlotinib, everolimus, gefitinib, lapatinib, ramucirumab, panitumumab, pazopanib, pertuzumab, nivolumab, regorafenib, lenvatinib, sorafenib, sunitinib, temsirolimus, trastuzumab, and pharmaceutically acceptable salts or derivatives thereof.

Further, radioisotopes such as $^{211}At$, $^{131}I$, $^{125}I$, $^{90}Y$, $^{186}Re$, $^{188}Re$, $^{153}Sm$, $^{212}Bi$, $^{32}P$, $^{175}Lu$, and $^{176}Lu$, which are known in literatures and the like, may also be used as antitumor agents. The radioisotopes are desirably those effective for treating and diagnosing tumors, and such radioisotopes may also be composed in the pharmaceutical composition for treating and/or preventing cancer according to the present invention.

<Treatment and Prevention Methods>

The present invention further provides a method for treating and/or preventing cancer in a subject who suffers (or has suffered) from a cancer, comprising administering the pharmaceutical composition for treating and/or preventing cancer according to the present invention, or a combination drug comprising the pharmaceutical composition for treating and/or preventing cancer according to the present invention and the above-described another antitumor agent (or a pharmaceutical composition comprising the antitumor agent), to the subject.

The terms "treating cancer" and "antitumor effects" used herein refer to the effects on cancer cells or tumors, compared with a negative control which is not treated with the polynucleotide of the present invention or the pharmaceutical composition for treating and/or preventing cancer according to the present invention, wherein the effects include not only complete inhibition of the growth of cancer cells and regression or disappearance of tumors, but also delay in the increase of cancer cells (i.e., reduction in the increment of cancer cells) or delay in the tumor growth compared with a negative control which is not treated with the polynucleotide of the present invention or the pharmaceutical composition for treating and/or preventing cancer according to the present invention.

The term "prevention" used herein also includes prevention of cancer recurrence for reducing a risk of recurrence after cancer treatment by cancer therapy such as surgery, chemotherapy, radiotherapy, or immunotherapy.

The above descriptions of pharmaceutical composition, combination drug, polynucleotide as active ingredient, dose, usage, dosage form, and cancers to be targeted, and the like also apply to the methods of this section.

EXAMPLES

The present invention will be more specifically described in reference to the following Examples. However, these examples are not intended to limit the scope of the present invention.

[Example 1] Effectiveness of Synthetic RNAs on Pancreatic Cancer Cells

A synthetic RNA having (i.e., consisting of; the same applies to the word regarding the sequences in the present description) the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15, were each evaluated for the effectiveness on pancreatic cancer cells.

A Panc-1 cell line (ATCC® CRL-1469™) as pancreatic cancer cells was seeded in a DMEM medium (Nacalai Tesque, Japan) supplemented with 10% FBS, and was then cultured under conditions of 37° C. and 5% $CO_2$. Panc-1 pancreatic cancer cells were seeded at $6 \times 10^3$ cells per well in 96-well plates. Thereafter, the RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14 or SEQ ID NO: 15 or a negative control oligo (Thermo Fisher Scientific Inc., mirVana™ miRNA Mimic, Negative Control) was added at a concentration of 30 nM and introduced into the pancreatic cancer cells, using Lipofectamine RNAiMAX (Thermo Fisher Scientific Inc.). The culture medium was exchanged 24 hours after the gene introduction, and the number of cells was measured for 5 days. The number of cells was determined by measuring ATP activity using the Celtiter-glo (Promega Corporation) reagent, and the measurement value was used as an indicator of the number of surviving cells. The results are shown in FIG. 1. The evaluation test was carried out at n=3. The graph of FIG. 1 indicates the mean±standard deviation of the viability (%) of the pancreatic cancer cells compared with the negative control.

As a result, the Panc-1 cell line cells into which the RNA synthetic products having the nucleotide sequences as set forth in SEQ ID NOs: 12 to 15 had been introduced, were found to have cell viability of 39%, 56%, 77% and 66%, respectively, compared with pancreatic cancer cells into which the negative control oligo had been introduced.

[Example 2] Effectiveness of Synthetic RNAs on Breast Cancer Cells

A synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 were each evaluated for the effectiveness on breast cancer cells.

Figure 2:
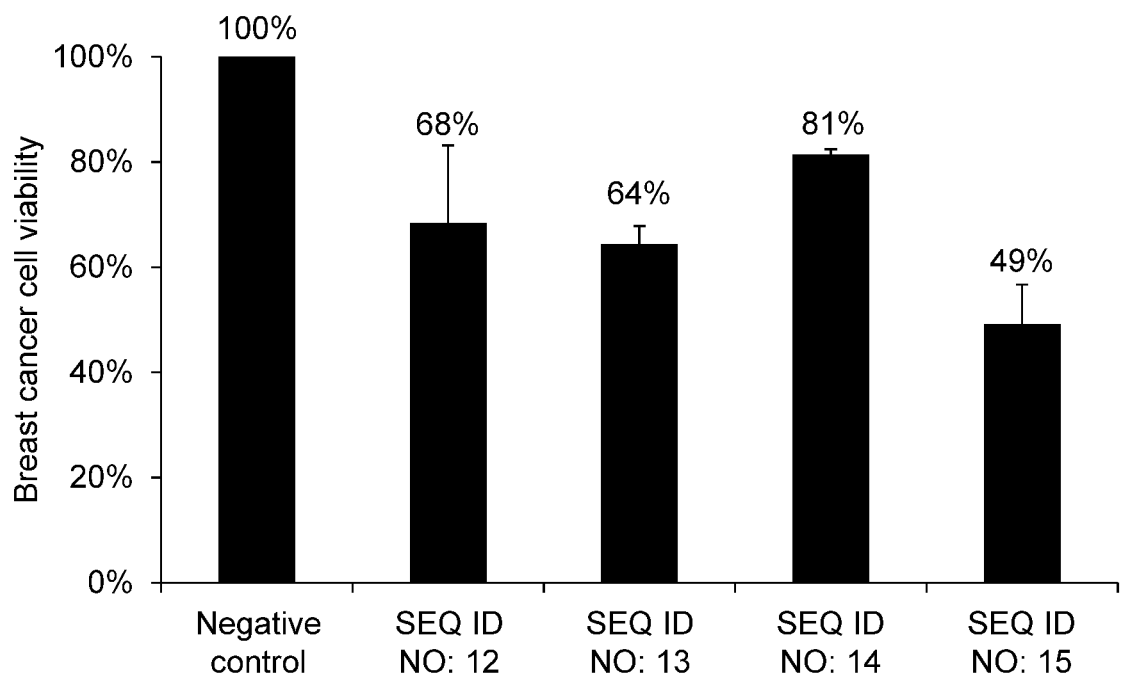
FIG. 2 This figure shows the ratios of viable cell counts (cell viability (%)) of the breast cancer cell line MCF-7 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 into the cancer cells, relative to the viable cell count (100%) after introduction of a synthetic RNA being a negative control oligo into the cancer cells.

An MCF-7 cell line (ATCC® HTB-22™) as breast cancer cells was seeded in an RPMI medium (Nacalai Tesque, Japan) supplemented with 10% FBS, and was then cultured under conditions of 37° C. and 5% $CO_2$. MCF-7 breast cancer cells were seeded at $6 \times 10^3$ cells per well in 96-well plates. Thereafter, the RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14 or SEQ ID NO: 15 or a negative control oligo (Thermo Fisher Scientific Inc., mirVana™ miRNA Mimic, Negative Control) was added at a concentration of 30 nM and introduced into the breast cancer cells, using Lipofectamine RNAiMAX (Thermo Fisher Scientific Inc.). The culture medium was exchanged 24 hours after the gene introduction, and the number of cells was measured for 5 days. The number of cells was determined by measuring ATP activity using the Celtiter-glo (Promega Corporation) reagent, and the measurement value was used as an indicator of the number of surviving cells. The results are shown in FIG. 2. The evaluation test was carried out at n=3. The graph of FIG. 2 indicates the mean±standard deviation of the viability (%) of the breast cancer cells compared with the negative control. As a result, breast cancer cells into which the RNA synthetic products having the nucleotide sequences as set forth in SEQ ID NOs: 12 to 15 had been introduced, were found to have cell viability of 68%, 64%, 81% and 49%, respectively, compared with breast cancer cells into which the negative control oligo had been introduced.

[Example 3] Effectiveness of Synthetic RNAs on Lung Cancer Cells

A synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 were each evaluated for the effectiveness on lung cancer cells.

Figure 3:
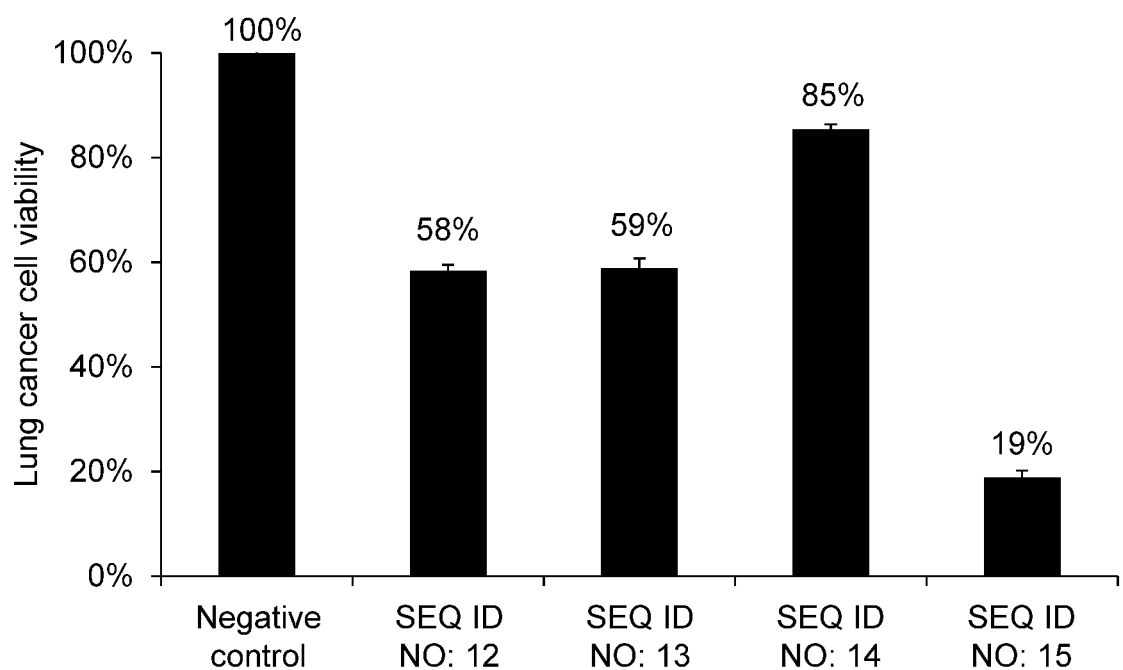
FIG. 3 This figure shows the ratios of viable cell counts (cell viability (%)) of the lung cancer cell line A549 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 into the cancer cells, relative to the viable cell count (100%) after introduction of a synthetic RNA being a negative control oligo into the cancer cells.

An A549 cell line (ATCC® CCL-185™) as lung cancer cells was seeded in an RPMI medium (Nacalai Tesque, Japan) supplemented with 10% FBS, and was then cultured under conditions of 37° C. and 5% $CO_2$. A549 lung cancer cells were seeded at $3 \times 10^3$ cells per well in 96-well plates. Thereafter, the RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14 or SEQ ID NO: 15 or a negative control oligo (Thermo Fisher Scientific Inc., mirVana™ miRNA Mimic, Negative Control) was added at a concentration of 30 nM and introduced into the lung cancer cells, using Lipofectamine RNAiMAX (Thermo Fisher Scientific Inc.). The culture medium was exchanged 24 hours after the gene introduction, and the number of cells was measured for 5 days. The number of cells was determined by measuring the ATP activity using the Celtiter-glo (Promega Corporation) reagent, and the measurement value was used as an indicator of the number of surviving cells. The results are shown in FIG. 3. The evaluation test was carried out at n=3. The graph of FIG. 3 indicates the mean±standard deviation of the the viability (%) of the lung cancer cells compared with the negative control. As a result, lung cancer cells into which the RNA synthetic products having the nucleotide sequences as set forth in SEQ ID NOs: 12 to 15 had been introduced, were found to have cell viability of 58%, 59%, 85% and 19%, respectively, compared with lung cancer cells, into which the negative control oligo had been introduced.

[Example 4] Effectiveness of Synthetic RNAs on Stomach Cancer Cells

A synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, a synthetic RNA having the same nucleotide sequence as hsa-miR-6841-3p as set forth in SEQ ID NO: 15, and a synthetic RNA having the same nucleotide sequence as hsa-miR-4645-5p as set forth in SEQ ID NO: 20 were each evaluated for the effectiveness on stomach cancer cells.

Figure 4:
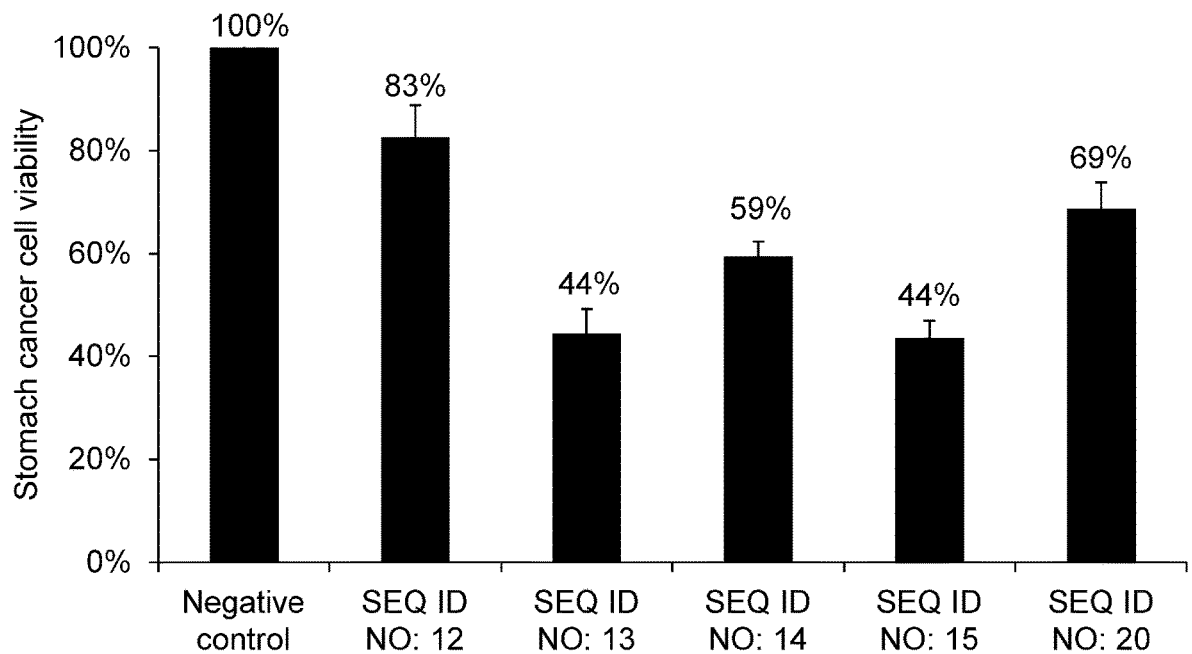
FIG. 4 This figure shows the ratios of viable cell counts (cell viability (%)) of the stomach cancer cell line NC1-N87 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, a synthetic RNA having the same nucleotide sequence as hsa-miR-6841-3p as set forth in SEQ ID NO: 15, and a synthetic RNA having the same nucleotide sequence as hsa-miR-4645-5p as set forth in SEQ ID NO: 20 into the cancer cells, relative to the viable cell count (100%) of after introduction of a synthetic RNA being a negative control oligo into the cancer cells.

An NC1-N87 cell line (ATCC® CRL-5822™) as stomach cancer cells was seeded in an RPMI medium (Nacalai Tesque, Japan) supplemented with 10% FBS, and was then cultured under conditions of 37° C. and 5% $CO_2$. The stomach cancer cells were seeded at $6 \times 10^3$ cells per well in 96-well plates. Thereafter, an RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14, SEQ ID NO: 15 or SEQ ID NO: 20 or a negative control oligo (Thermo Fisher Scientific Inc., mirVana™ miRNA Mimic, Negative Control) was added at a concentration of 30 nM and introduced into the stomach cancer cells, using Lipofectamine RNAiMAX (Thermo Fisher Scientific Inc.). The culture medium was exchanged 24 hours after the gene introduction and the number of cells was measured for 5 days. The number of cells was determined by measuring the ATP activity using the Celtiter-glo (Promega Corporation) reagent, and the measurement value was used as an indicator of the number of surviving cells. The results are shown in FIG. 4. The evaluation test was carried out at n=3. and The graph of FIG. 4 indicates the mean±standard deviation of the viability (%) of the stomach cancer cells compared with the negative control. As a result, the stomach cancer cells into which the RNA synthetic products having the nucleotide sequences as set forth in SEQ ID NOs: 12 to 15 and 20 had been introduced, were found to have cell viability of 83%, 44%, 59%, 44% and 69%, respectively, compared with stomach cancer cells, into which the negative control oligo had been introduced.

[Example 5] Effectiveness of Synthetic RNAs on Liver Cancer Cells

A synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, and a synthetic RNA having the same nucleotide sequence as hsa-miR-6841-3p as set forth in SEQ ID NO: 15 were each evaluated for the effectiveness on liver cancer cells.

Figure 5:
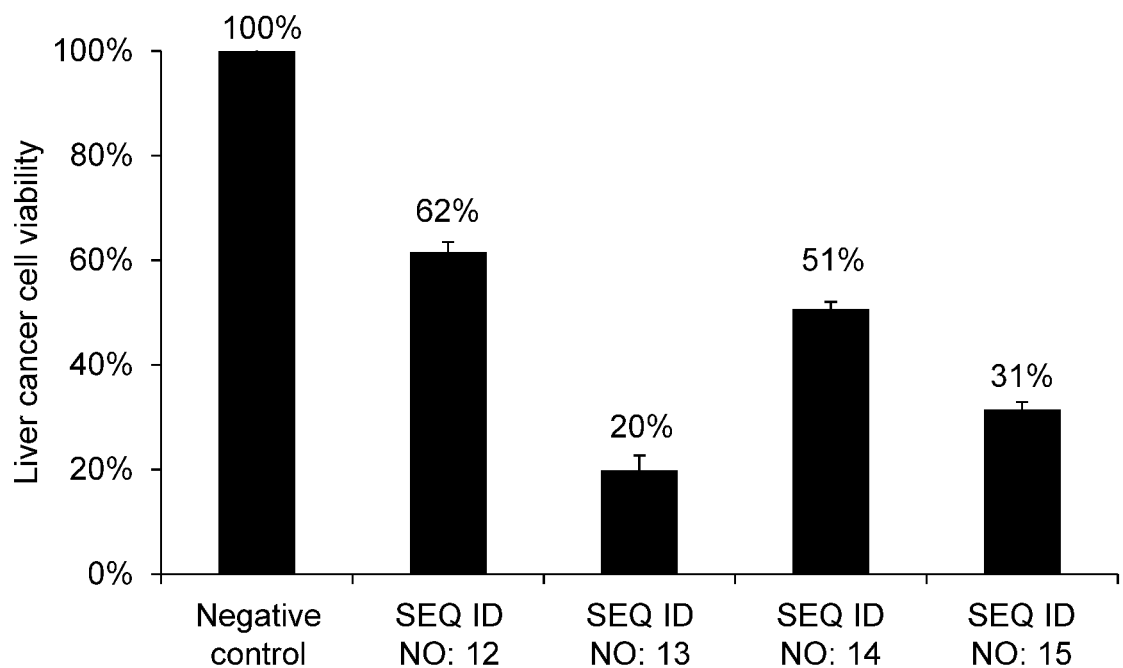
FIG. 5 This figure shows the ratios of viable cell counts (cell viability (%)) of the liver cancer cell line HepG2 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14 into the cancer cells, and a synthetic RNA having the same nucleotide sequence as hsa-miR-6841-3p as set forth in SEQ ID NO: 15, relative to the viable cell count (100%) after introduction of a synthetic RNA being a negative control oligo into the cancer cells.

A HepG2 cell line (ATCC® HB-8065™) as liver cancer cells was seeded in an RPMI medium (Nacalai Tesque, Japan) supplemented with 10% FBS, and was then cultured under conditions of 37° C. and 5% $CO_2$. The liver cancer cells were seeded at $6 \times 10^3$ cells per well in 96-well plates. Thereafter, an RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14 or SEQ ID NO: 15 or a negative control oligo (Thermo Fisher Scientific Inc., mirVana™ miRNA Mimic, Negative Control) was added at a concentration of 30 nM and introduced into the liver cancer cells, using Lipofectamine RNAiMAX (Thermo Fisher Scientific Inc.). The culture medium was exchanged 24 hours after the gene introduction, and the number of cells was measured for 5 days. The number of cells was determined by measuring ATP activity using the Celtiter-glo (Promega Corporation) reagent, and the measurement value was used as an indicator of the number of surviving cells. The results are shown in FIG. 5. The evaluation test was carried out at n=3. The graph of FIG. 5 indicates the mean±standard deviation of the viability (%) of the liver cancer cells compared with the negative control. As a result, the liver cancer cells into which the RNA synthetic products having the nucleotide sequences as set forth in SEQ ID NOs: 12 to 15 had been introduced, were found to have cell viability of 62%, 20%, 51% and 31%, respectively, compared with liver cancer cells into which the negative control oligo had been introduced.

[Example 6] Effectiveness of Synthetic RNAs on Colorectal Cancer Cells (1)

A synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, a synthetic RNA having the same nucleotide sequence as hsa-miR-6841-3p as set forth in SEQ ID NO: 15, and a synthetic RNA having the same nucleotide sequence as hsa-miR-4645-5p as set forth in SEQ ID NO: 20 were each evaluated for the effectiveness on colorectal cancer cells.

Figure 6:
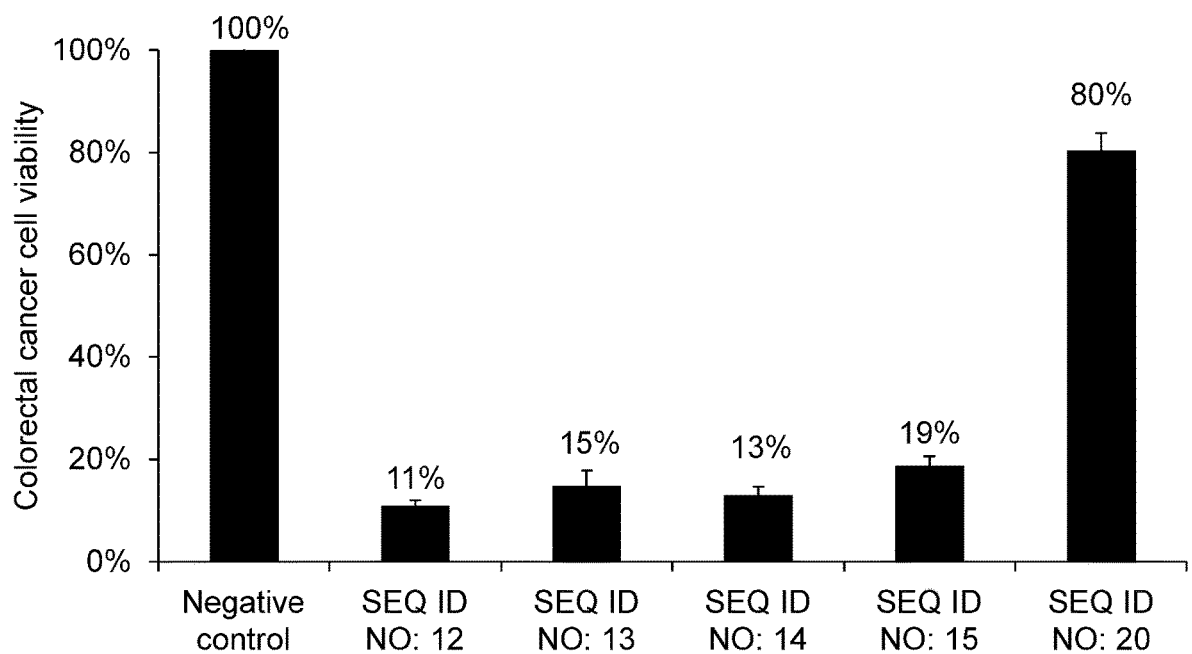
FIG. 6 This figure shows the ratios of viable cell counts (cell viability (%)) of the colorectal cancer cell line HCT116 after introduction of a synthetic RNA having the same nucleotide sequence as hsa-miR-8073 as set forth in SEQ ID NO: 12, a synthetic RNA having the same nucleotide sequence as hsa-miR-221-5p as set forth in SEQ ID NO: 13, a synthetic RNA having the same nucleotide sequence as hsa-miR-4722-3p as set forth in SEQ ID NO: 14, a synthetic RNA having the same nucleotide sequence as hsa-miR-6841-3p as set forth in SEQ ID NO: 15, and a synthetic RNA having the same nucleotide sequence as hsa-miR-4645-5p as set forth in SEQ ID NO: 20 into the cancer cells, relative to the viable cell count (100%) after introduction of a synthetic RNA being a negative control oligo into the cancer cells.

An HCT116 cell line (ATCC® CCL-247™) as colorectal cancer cells was seeded in a McCoy's medium (Nacalai Tesque, Japan) supplemented with 10% FBS, and was then cultured under conditions of 37° C. and 5% $CO_2$. HCT116 colorectal cancer cells were seeded at $6 \times 10^3$ cells per well in 96-well plates. Thereafter, an RNA synthetic product (Thermo Fisher Scientific Inc., mirVana™ miRNA Mimics) having the nucleotide sequence as set forth in SEQ ID NO: 12, SEQ ID NO: 13, SEQ ID NO: 14, SEQ ID NO: 15 or SEQ ID NO: 20 or a negative control oligo (Thermo Fisher Scientific Inc., mirVana™ miRNA Mimic, Negative Control) was added at a concentration of 30 nM and introduced into the colorectal cancer cells, using Lipofectamine RNAiMAX (Thermo Fisher Scientific Inc.). The culture medium was exchanged 24 hours after the gene introduction, and the number of cells was measured for 5 days. The number of cells was determined by measuring the ATP activity using the Celtiter-glo (Promega Corporation) reagent, and the measurement value was used as an indicator of the number of surviving cells. The results are shown in FIG. 6. The evaluation test was carried out at n=3. The graph of FIG. 6 indicates the mean±standard deviation of the viability (%) of the colorectal cancer cells compared with the negative control. As a result, colorectal cancer cells into which the RNA synthetic products having the nucleotide sequences as set forth in SEQ ID NOs: 12 to 15 and 20 had been introduced, were found to have cell viability of 11%, 15%, 13%, 19% and 80%, respectively, compared with colorectal cancer cells, into which the negative control oligo had been introduced.

[Example 7] Effectiveness of Synthetic RNAs on Colorectal Cancer Cells (2)

A synthetic RNA having the nucleotide sequence as set forth in SEQ ID NO: 16 (a nucleotide sequence in which SEQ ID NO: 7, namely, a nucleotide sequence ranging from positions 9 to 22 counted from the 5'-terminus of SEQ ID NO: 14, is added to the 3'-terminal side of SEQ ID NO: 1), a synthetic RNA having the nucleotide sequence as set forth in SEQ ID NO: 17 (a nucleotide sequence in which a nucleotide sequence (SEQ ID NO: 9) ranging from positions 9 to 20 counted from the 5'-terminus of hsa-miR-4454 as set forth in SEQ ID NO: 23, is added to the 3'-terminal side of SEQ ID NO: 1, namely, a nucleotide sequence ranging from positions 1 to 8 counted from the 5'-terminus of SEQ ID NO: 12), a synthetic RNA having the nucleotide sequence as set forth in SEQ ID NO: 18 (a nucleotide sequence in which SEQ ID NO: 7, namely, a nucleotide sequence ranging from positions 9 to 22 counted from the 5'-terminus of SEQ ID NO: 14, is added to the 3'-terminal side of SEQ ID NO: 3), a synthetic RNA having the nucleotide sequence as set forth in SEQ ID NO: 19 (a nucleotide sequence in which a nucleotide sequence (SEQ ID NO: 9) ranging from positions 9 to 20 counted from the 5'-terminus of SEQ ID NO: 23, is added to the 3'-terminal side of SEQ ID NO: 3, namely, the 3'-terminal side of a nucleotide sequence ranging from positions 1 to 8 counted from the 5'-terminus of SEQ ID NO: 15), a synthetic RNA having the nucleotide sequence as set forth in SEQ ID NO: 21 (a nucleotide sequence in which a nucleotide sequence (SEQ ID NO: 11) formed by adding a nucleotide sequence CUC to the 3'-terminal side of a nucleotide sequence ranging from positions 9 to 19 counted from the 5'-terminus of SEQ ID NO: 20, is added to the 3'-terminal side of SEQ ID NO: 4), a synthetic RNA having the nucleotide sequence as set forth in SEQ ID NO: 22 (a nucleotide sequence in which a nucleotide sequence (SEQ ID NO: 5) ranging from positions 9 to 22 counted from the 5'-terminus of SEQ ID NO: 12, is added to the 3'-terminal side of SEQ ID NO: 4, namely, a nucleotide sequence ranging from positions 1 to 8 from the 5'-terminus of SEQ ID NO: 20), and a synthetic RNA having the same nucleotide sequence as hsa-miR-4454 as set forth in SEQ ID NO: 23 known as a cancer marker (Thermo Fisher Scientific Inc., mirVana™ miRNA Mimics) were each evaluated for the effectiveness on colorectal cancer, by the same method as that described in Example 6.

Figure 7:
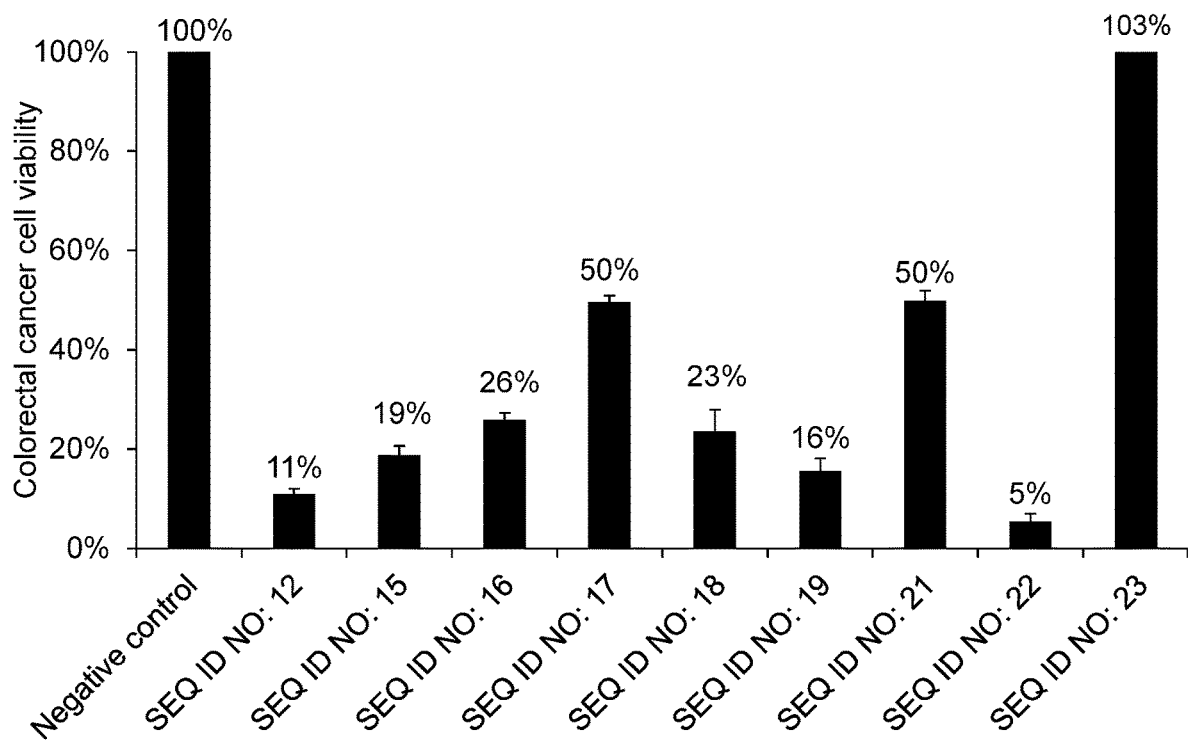
FIG. 7 This figure shows the ratios of viable cell counts of the colorectal cancer cell line HCT116 after introduction of a synthetic RNA having the same nucleotide sequence as hsa-miR-8073 as set forth in SEQ ID NO: 12 (present invention), a synthetic RNA having the nucleotide sequence as hsa-miR-6841-3p as set forth in SEQ ID NO: 15 (present invention), a synthetic RNA having the nucleotide sequence as set forth in SEQ ID NO: 16 (present invention), a synthetic RNA having the nucleotide sequence as set forth in SEQ ID NO: 17 (present invention), a synthetic RNA having the nucleotide sequence as set forth in SEQ ID NO: 18 (present invention), a synthetic RNA having the nucleotide sequence as set forth in SEQ ID NO: 19 (present invention), a synthetic RNA having the nucleotide sequence as set forth in SEQ ID NO: 21 (present invention), a synthetic RNA having the nucleotide sequence as set forth in SEQ ID NO: 22 (present invention), and a synthetic RNA having the same nucleotide sequence as hsa-miR-4454 as set forth in SEQ ID NO: 23 (comparative example) into the cancer cells, relative to the viable cell count (100%) after introduction of a synthetic RNA being a negative control oligo into the cancer cells (with the cell viabilities of 11%, 19%, 26%, 50%, 23%, 16%, 50%, 5% and 103%, respectively).

As a result, colorectal cancer cells into which the RNA synthetic products having the nucleotide sequences as set forth in SEQ ID NOs: 16, 17, 18, 19, 21 and 22 had been introduced, and colorectal cancer cells into which the RNA synthetic products having the nucleotide sequences as set forth in SEQ ID NOs: 12 and 15 had been introduced (Example 6), were found to have cell viability of 50% or less. In contrast, the cell viability of colorectal cancer cells into which the RNA synthetic product having the nucleotide sequence as set forth in SEQ ID NO: 23 had been introduced, was 103%, and thus, the RNA synthetic product having the nucleotide sequence as set forth in SEQ ID NO: 23 was hardly effective. The results are shown in FIG. 7.

All of the synthetic RNAs consisting of the nucleotide sequences as set forth in SEQ ID NOs: SEQ ID NOs: 12, 16 and 17, each of which comprises the nucleotide sequence as set forth in SEQ ID NO: 1 at the 5'-terminus thereof; and consisting of the nucleotide sequences as set forth in SEQ ID NOs: SEQ ID NOs: 15, 18 and 19, each of which comprises the nucleotide sequence as set forth in SEQ ID NO: 3 at the 5'-terminus thereof; and consisting of the nucleotide sequences as set forth in SEQ ID NOs: SEQ ID NOs: 21 and 22, each of which comprises the nucleotide sequence as set forth in SEQ ID NO: 4 at the 5'-terminus thereof, significantly reduced the cell viability of colorectal cancer cells. The synthetic RNA having the nucleotide sequence as set forth in SEQ ID NO: 23, which has the same sequence on the 3'-terminal side as those of SEQ ID NOs: 17 and 19, did not exhibit effectiveness. Accordingly, it was shown that the nucleotide sequence on the 5'-terminal side (in particular, the nucleotide sequence ranging from positions 1 to 8 counted from the 5'-terminus) is important for anticancer effects.

[Comparative Example 1] Effectiveness of Synthetic RNAs on Colorectal Cancer Cells A synthetic RNA having the same nucleotide sequence as hsa-miR-575 (miRBase Accession No. MIMAT0003240) as set forth in SEQ ID NO: 24 known as a cancer marker and a synthetic RNA having the same nucleotide sequence as hsa-miR-1321 (miRBase Accession No. MIMAT0005952) as set forth in SEQ ID NO: 25, which is known to be associated with blood cancer (Thermo Fisher Scientific Inc., mirVana™ miRNA Mimics), were each evaluated for the effectiveness on colorectal cancer, by the same method as that described in Example 6.

Figure 8:
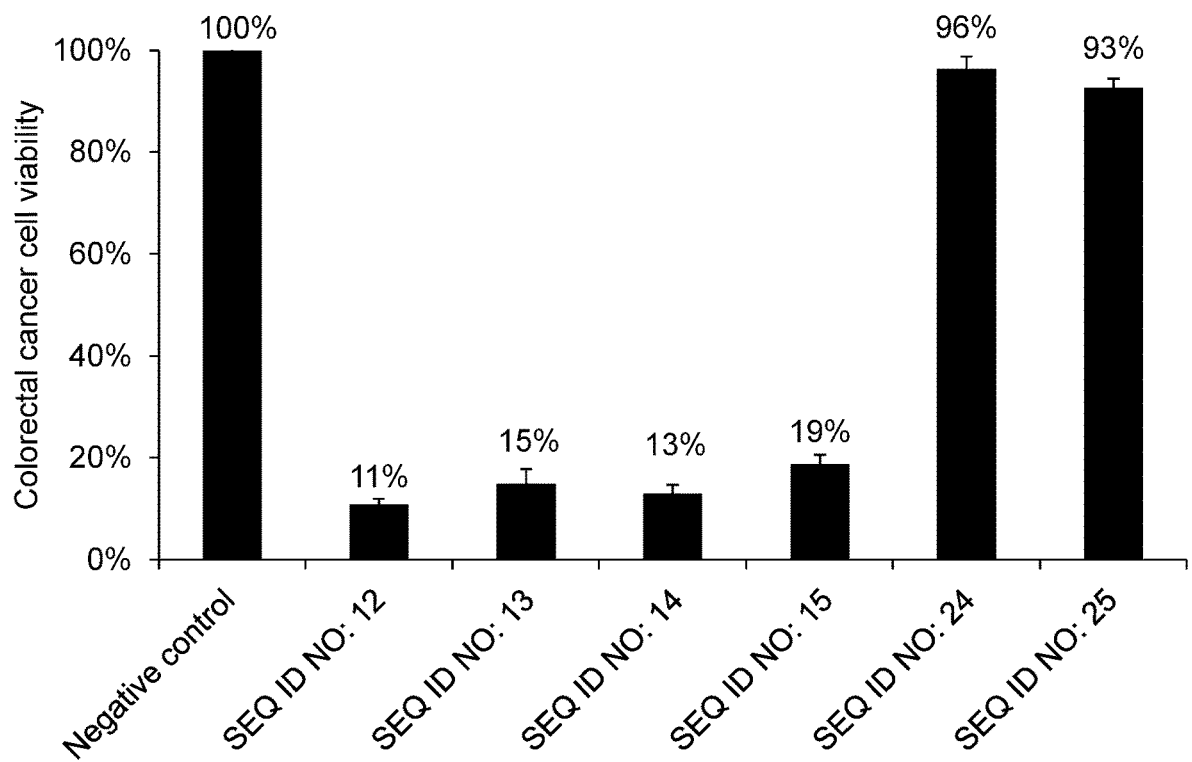
FIG. 8 This figure shows the ratios of viable cell counts of the colorectal cancer cell line HCT116 after introduction of a synthetic RNA having the same nucleotide sequence as hsa-miR-8073 as set forth in SEQ ID NO: 12 (present invention), a synthetic RNA having the same nucleotide sequence as hsa-miR-221-5p as set forth in SEQ ID NO: 13 (present invention), a synthetic RNA having the same nucleotide sequence as hsa-miR-4722-3p as set forth in SEQ ID NO: 14 (present invention), a synthetic RNA having the nucleotide sequence as hsa-miR-6841-3p as set forth in SEQ ID NO: 15 (present invention), a synthetic RNA having the same nucleotide sequence as hsa-miR-575 as set forth in SEQ ID NO: 24 (comparative example), and a synthetic RNA having the same nucleotide sequence as hsa-miR-1321 as set forth in SEQ ID NO: 25 (comparative example) into the cancer cells, relative to the viable cell count (100%) after introduction of a synthetic RNA being a negative control oligo into the cancer cells (with the cell viabilities of 11%, 15%, 13%, 19%, 96% and 93%, respectively).

As a result, colorectal cancer cells into which the RNA synthetic products having the nucleotide sequences as set forth in SEQ ID NOs: SEQ ID NOs: 12 to 15 had been introduced, were found to have cell viability of 20% or less. In contrast, colorectal cancer cells into which the RNA synthetic products having the nucleotide sequences as set forth in SEQ ID NOs: 24 and 25 had been introduced, were found to have cell viability of 96% and 93%, respectively. The results are shown in FIG. 8.

[Comparative Example 2] Influence of Synthetic RNA on Normal Cells

The influence of a synthetic RNA having the nucleotide sequence as set forth in SEQ ID NO: 12 (Thermo Fisher Scientific Inc. mirVana™ miRNA Mimics) on mammary epithelial cells, which are normal cells, was evaluated.

A 184B5 cell line (ATCC® CRL-8799™) as mammary epithelial cells was seeded in an MEBM medium (Lonza) supplemented with BPE, hydrocortisone, hEGF and insulin, and was then cultured under conditions of 37° C. and 5% $CO_2$. The cells were seeded at $6 \times 10^3$ cells per well in 96-well plates. Thereafter, an RNA synthetic product having the nucleotide sequence as set forth in SEQ ID NO: 12 or a negative control oligo (Thermo Fisher Scientific Inc. mirVana™ miRNA Mimic, Negative Control) was added at a concentration of 3 nM and introduced into the cells, using Lipofectamine RNAiMAX (Thermo Fisher Scientific Inc.). The culture medium was exchanged 24 hours after the gene introduction, and the number of cells was measured for 5 days. The number of cells was determined by measuring ATP activity using the Celtiter-glo (Promega Corporation) reagent, and the measurement value was used as an indicator of the number of surviving cells. As a control, the same experiment as described above was carried out using the breast cancer cell line MCF-7, instead of the mammary epithelial cell line 184B5.

Figure 9:
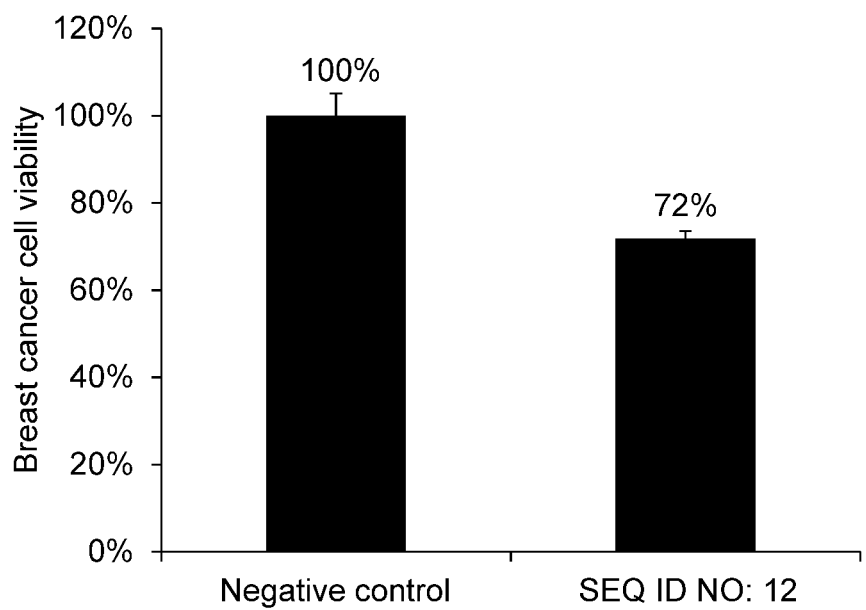
FIG. 9 This figure shows (A) the ratio of viable cell count (cell viability: 72%) of the breast cancer cell line MCF-7 after introduction of a synthetic RNA (3 nM) having the same nucleotide sequence as hsa-miR-8073 as set forth in SEQ ID NO: 12 into the cancer cells, relative to the viable cell count (100%) after introduction of a synthetic RNA being a negative control oligo into the cancer cells; and (B) the ratio of viable cell count (cell viability: 102%) of the mammary epithelial cell line 184B5 after introduction of a synthetic RNA (3 nM) having the same nucleotide sequence as hsa-miR-8073 as set forth in SEQ ID NO: 12 into normal cells, relative to the viable cell count (100%) after introduction of a synthetic RNA being a negative control oligo into normal cells.
Figure 9:
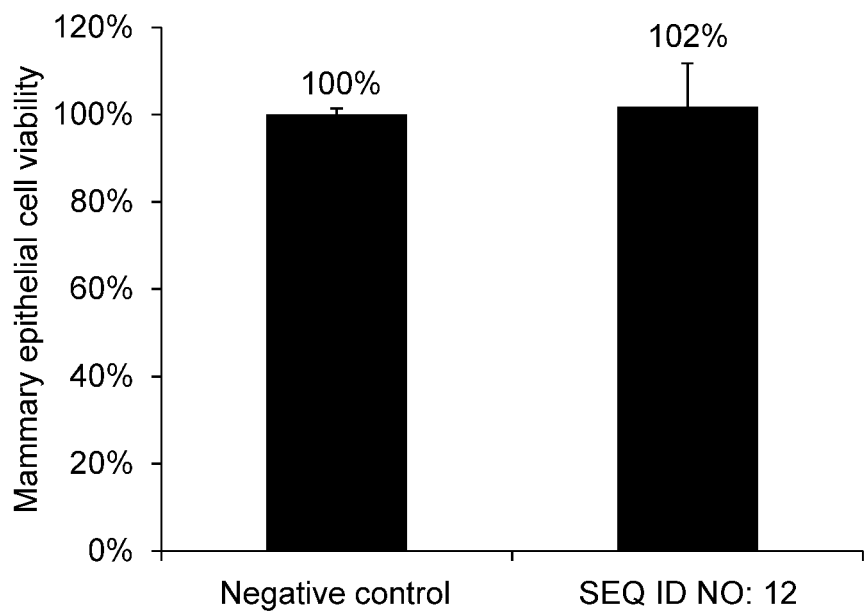

The results are shown in FIG. 9. The evaluation test was carried out at n=3. The graph of FIG. 9 indicates the mean±standard deviation of the viability (%) of the pancreatic cancer cells compared with the negative control. As a result, the mammary epithelial cells was found to have the cell viability of 102%, whereas the breast cancer cell line MCF-7 was found to have the cell viability of 72% (FIG. 9A), when the RNA synthetic product (3 nM) having the nucleotide sequence as set forth in SEQ ID NO: 12 was introduced thereinto. Thus, the influence of the synthetic RNA on normal cells was not observed (FIG. 9B).

[Example 8] Effectiveness of Synthetic RNA on Cancer-Bearing Mouse Models

Using cancer-bearing mice into which a human-derived cancer cell line had been transplanted, the antitumor effects of a synthetic RNA having the same nucleotide sequence as hsa-miR-8073 as set forth in SEQ ID NO: 12 were examined.

A human colorectal cancer cell line HCT116 (ATCC® CCL-247™) was subcutaneously transplanted into the back of six Balb/c nude mice (Charles River Japan Inc.) at $5 \times 10^6$ cells per mouse, and the tumor was grown until its diameter reached about 5 mm. To each of the six cancer-bearing mice, a mixed solution of a synthetic RNA having the nucleotide sequence as set forth in SEQ ID NO: 12 (Thermo Fisher Scientific Inc., mirVana™ miRNA Mimics) or a negative control oligo (Thermo Fisher Scientific Inc., mirVana™ miRNA Mimic, Negative Control) (2 nmol per mouse) and 50 µl of 0.5% AteloGene Local Use (KOKEN CO., LTD.) was subcutaneously administered around the tumor. Subsequently, the mixed solution of the synthetic RNA and 0.5% AteloGene Local Use was subcutaneously administered at the same dose every 2 days, 3 times in total, around the tumor of the cancer-bearing mouse, and the size of the tumor was measured once every two days. The size of the tumor was calculated as a volume, using the formula: 0.5×(long diameter×short diameter×short diameter).

Figure 10:
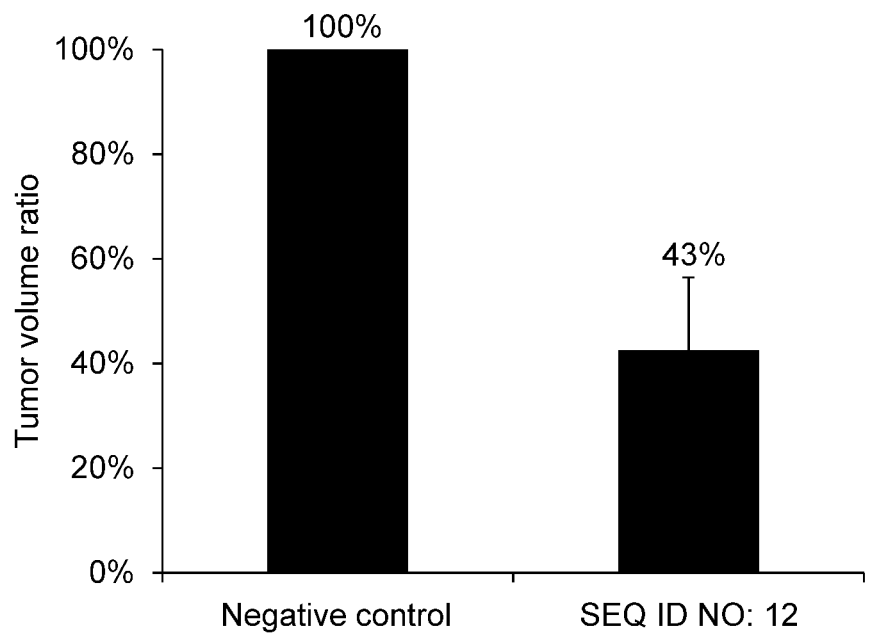
FIG. 10 This figure shows (B) changes in tumor volume for 13 days and (A) the tumor volume ratio on day 13, after the administration of a synthetic RNA having the same nucleotide sequence as hsa-miR-8073 as set forth in SEQ ID NO: 12 or a synthetic RNA being a negative control oligo to tumor-bearing mice.
Figure 10:
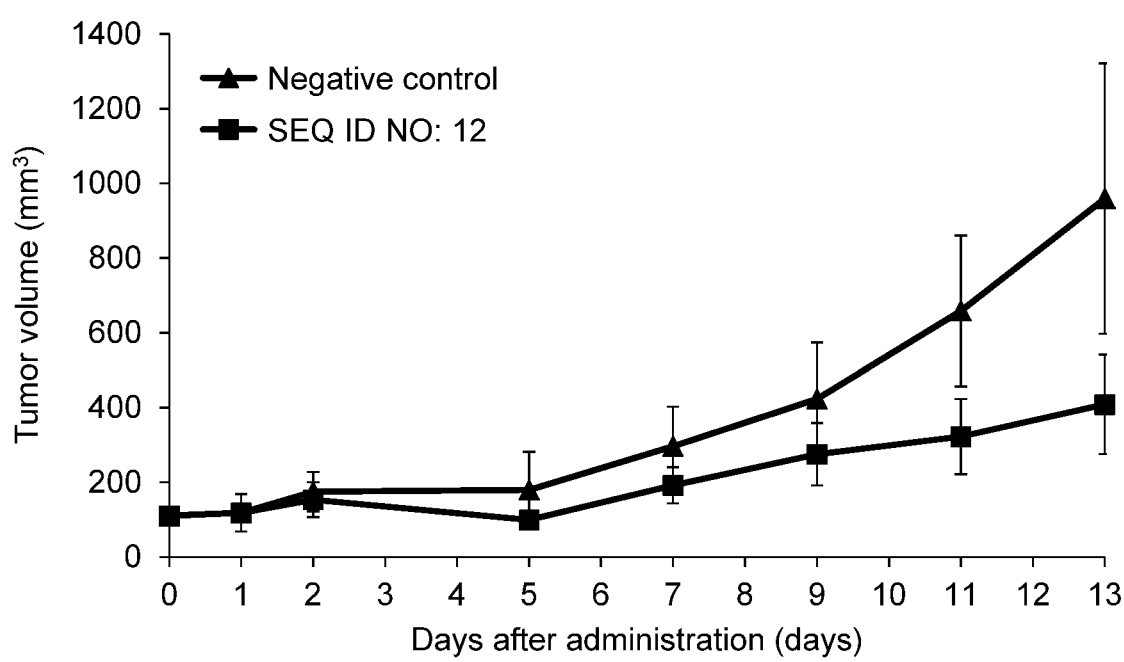

As a result, 13 days after the initial administration, the tumor volume ratio of the test group to which the synthetic RNA having the same nucleotide sequence as SEQ ID NO: 12 had been administered was 43%, relative to the tumor volume of the negative control group (to which the negative control oligo had been administered) set at 100% (FIG. 10A). In addition, changes in the tumor volume for 13 days after the administration of the synthetic RNA to the cancer-bearing mice are shown in FIG. 10B.

From these results, it was shown that the synthetic RNA having the nucleotide sequence as SEQ ID NO: 12 exhibits antitumor effects in vivo on cancer cells.

INDUSTRIAL APPLICABILITY

The pharmaceutical composition for treating cancer according to the present invention is useful for treating and/or preventing cancer.

All publications, patents, and patent applications cited in the present description are incorporated herein by reference in their entirety.

The invention claimed is:

1. A method for treating cancer in a subject in need thereof, comprising administering to the subject a pharmaceutical composition comprising a polynucleotide as an active ingredient, wherein said polynucleotide comprises:
   (i) a nucleotide sequence of the following (a) or (b) as a nucleotide sequence on the 5'-terminal side:
      (a) the nucleotide sequence as set forth in SEQ ID NO: 1, or
      (b) a nucleotide sequence comprising a substitution of one nucleotide in the nucleotide sequence as set forth in SEQ ID NO: 1; and
   (ii) a nucleotide sequence of the following (c) or (d) on the 3'-terminal side of the nucleotide sequence of (i):
      (c) the nucleotide sequence as set forth in any one of SEQ ID NOs: 5, 7 to 9, and 11, or
      (d) a nucleotide sequence comprising a deletion, substitution, insertion, and/or addition of 1 or 2 nucleotides in the nucleotide sequence as set forth in any one of SEQ ID NOs: 5, 7 to 9, and 11, and wherein said polynucleotide is 18 to 28 nucleotides in length.

2. The method according to claim 1, wherein the nucleotide sequence of (b) is a nucleotide sequence comprising a substitution of any one of nucleotides at positions 4 to 6 from the 5'-terminus of the nucleotide sequence as set forth in SEQ ID NO: 1.

3. The method according to claim 1, wherein the polynucleotide is a polynucleotide comprising the nucleotide sequence as set forth in any one of SEQ ID NOs: 1 to 4 as a nucleotide sequence on the 5'-terminal side.

4. The method according to claim 1, wherein the polynucleotide comprises a nucleotide sequence as set forth in any one of SEQ ID NOs: 12, 14 to 19, 21, and 22.

5. The method according to claim 1, wherein the polynucleotide is single stranded or double stranded.

6. The method according to claim 1, wherein the polynucleotide is RNA.

7. The method according to claim 1, wherein the cancer is a solid cancer.

8. The method according to claim 1, wherein the cancer is selected from the group consisting of breast cancer, kidney cancer, pancreatic cancer, colorectal cancer, lung cancer, brain tumors, stomach cancer, cervical cancer, ovarian cancer, prostate cancer, bladder cancer, esophagus cancer, liver cancer, fibrosarcomas, mast cell tumors, and melanomas.

9. The method according to claim 1, wherein the polynucleotide is inserted into a vector in an expressible manner in the form of DNA.

10. The method according to claim 1, wherein the polynucleotide is encapsulated into a carrier selected from the group consisting of non-cationic polymer carriers, liposome carriers, dendritic carriers, nano-material carriers, microparticle carriers, biostructural carriers, micelle carriers, polymer microparticles, and magnetic microparticles; or the polynucleotide is bound to the carrier.

11. A method for treating cancer in a subject in need thereof, comprising administering to the subject a combination drug comprising a pharmaceutical composition and an antitumor agent, wherein the pharmaceutical composition comprises a polynucleotide as an active ingredient,
wherein said polynucleotide comprises:
(i) a nucleotide sequence of the following (a) or (b) as a nucleotide sequence on the 5'-terminal side:
(a) the nucleotide sequence as set forth in SEQ ID NO: 1, or
(b) a nucleotide sequence comprising a substitution of one nucleotide in the nucleotide sequence as set forth in SEQ ID NO: 1; and
(ii) a nucleotide sequence of the following (c) or (d) on the 3'-terminal side of the nucleotide sequence of (i):
(c) the nucleotide sequence as set forth in any one of SEQ ID NOs: 5, 7 to 9, and 11, or
(d) a nucleotide sequence comprising a deletion, substitution, insertion, and/or addition of 1 or 2 nucleotides in the nucleotide sequence as set forth in any one of SEQ ID NOs: 5, 7 to 9, and 11,
and wherein said polynucleotide is 18 to 28 nucleotides in length.

* * * * *

SEQUENCE LISTING

```
<160> NUMBER OF SEQ ID NOS: 25

<210> SEQ ID NO 1
<211> LENGTH: 8
<212> TYPE: RNA
<213> ORGANISM: Homo sapiens

<400> SEQUENCE: 1 accuggca                                                                 8

<210> SEQ ID NO 2
<211> LENGTH: 8
<212> TYPE: RNA
<213> ORGANISM: Homo sapiens

<400> SEQUENCE: 2 accugcca                                                                 8

<210> SEQ ID NO 3
<211> LENGTH: 8
<212> TYPE: RNA
<213> ORGANISM: Homo sapiens

<400> SEQUENCE: 3 accuugca                                                                 8

<210> SEQ ID NO 4
<211> LENGTH: 8
<212> TYPE: RNA
```

```
<213> ORGANISM: Homo sapiens

<400> SEQUENCE: 4 accaggca                                                                  8

<210> SEQ ID NO 5
<211> LENGTH: 14
<212> TYPE: RNA
<213> ORGANISM: Homo sapiens

<400> SEQUENCE: 5
gcagggagcg ucgu                                                          14

<210> SEQ ID NO 6
<211> LENGTH: 14
<212> TYPE: RNA
<213> ORGANISM: Homo sapiens

<400> SEQUENCE: 6
uacaauguag auuu                                                          14

<210> SEQ ID NO 7
<211> LENGTH: 14
<212> TYPE: RNA
<213> ORGANISM: Homo sapiens

<400> SEQUENCE: 7
gcaccucccu gcag                                                          14

<210> SEQ ID NO 8
<211> LENGTH: 13
<212> TYPE: RNA
<213> ORGANISM: Homo sapiens

<400> SEQUENCE: 8
ucugcauccc cag                                                           13

<210> SEQ ID NO 9
<211> LENGTH: 12
<212> TYPE: RNA
<213> ORGANISM: Homo sapiens

<400> SEQUENCE: 9
gucacggcac ca                                                            12

<210> SEQ ID NO 10
<211> LENGTH: 11
<212> TYPE: RNA
<213> ORGANISM: Homo sapiens

<400> SEQUENCE: 10
agaaauauug u                                                             11

<210> SEQ ID NO 11
<211> LENGTH: 14
<212> TYPE: RNA
<213> ORGANISM: Homo sapiens

<400> SEQUENCE: 11
agaaauauug ucuc                                                          14

<210> SEQ ID NO 12
<211> LENGTH: 22
```

<212> TYPE: RNA
<213> ORGANISM: Homo sapiens

<400> SEQUENCE: 12
accuggcagc agggagcguc gu                                        22

<210> SEQ ID NO 13
<211> LENGTH: 22
<212> TYPE: RNA
<213> ORGANISM: Homo sapiens

<400> SEQUENCE: 13
accuggcaua caauguagau uu                                        22

<210> SEQ ID NO 14
<211> LENGTH: 22
<212> TYPE: RNA
<213> ORGANISM: Homo sapiens

<400> SEQUENCE: 14
accugccagc accucccugc ag                                        22

<210> SEQ ID NO 15
<211> LENGTH: 21
<212> TYPE: RNA
<213> ORGANISM: Homo sapiens

<400> SEQUENCE: 15
accuugcauc ugcaucccca g                                         21

<210> SEQ ID NO 16
<211> LENGTH: 22
<212> TYPE: RNA
<213> ORGANISM: Homo sapiens

<400> SEQUENCE: 16
accuggcagc accucccugc ag                                        22

<210> SEQ ID NO 17
<211> LENGTH: 20
<212> TYPE: RNA
<213> ORGANISM: Homo sapiens

<400> SEQUENCE: 17
accuggcagu cacggcacca                                           20

<210> SEQ ID NO 18
<211> LENGTH: 22
<212> TYPE: RNA
<213> ORGANISM: Homo sapiens

<400> SEQUENCE: 18
accuugcagc accucccugc ag                                        22

<210> SEQ ID NO 19
<211> LENGTH: 20
<212> TYPE: RNA
<213> ORGANISM: Homo sapiens

<400> SEQUENCE: 19
accuugcagu cacggcacca                                           20

<210> SEQ ID NO 20

```
<211> LENGTH: 19
<212> TYPE: RNA
<213> ORGANISM: Homo sapiens

<400> SEQUENCE: 20
accaggcaag aaauauugu                                                        19

<210> SEQ ID NO 21
<211> LENGTH: 22
<212> TYPE: RNA
<213> ORGANISM: Homo sapiens

<400> SEQUENCE: 21
accaggcaag aaauauuguc uc                                                    22

<210> SEQ ID NO 22
<211> LENGTH: 22
<212> TYPE: RNA
<213> ORGANISM: Homo sapiens

<400> SEQUENCE: 22
accaggcagc agggagcguc gu                                                    22

<210> SEQ ID NO 23
<211> LENGTH: 20
<212> TYPE: RNA
<213> ORGANISM: Homo sapiens

<400> SEQUENCE: 23
ggauccgagu cacggcacca                                                       20

<210> SEQ ID NO 24
<211> LENGTH: 19
<212> TYPE: RNA
<213> ORGANISM: Homo sapiens

<400> SEQUENCE: 24
gagccaguug gacaggagc                                                        19

<210> SEQ ID NO 25
<211> LENGTH: 18
<212> TYPE: RNA
<213> ORGANISM: Homo sapiens

<400> SEQUENCE: 25
cagggaggug aaugugau                                                         18
```